United States Patent [19]
Sessler et al.

[11] Patent Number: 6,072,038
[45] Date of Patent: *Jun. 6, 2000

[54] CONJUGATES OF TEXAPHYRINS

[75] Inventors: Jonathan L. Sessler, Austin, Tex.; Tarak D. Mody; Gregory W. Hemmi, both of Sunnyvale, Calif.

[73] Assignee: Board of Regents, The University of Texas System, Austin, Tex.

[ * ] Notice: This patent is subject to a terminal disclaimer.

[21] Appl. No.: 09/104,870

[22] Filed: Jun. 25, 1998

Related U.S. Application Data

[63] Continuation of application No. 08/795,393, Feb. 4, 1997, Pat. No. 5,888,997, which is a continuation-in-part of application No. 08/437,968, May 10, 1995, Pat. No. 5,622,946, which is a continuation of application No. PCT/US94/11491, Oct. 12, 1994, which is a continuation-in-part of application No. 08/135,118, Oct. 12, 1993, Pat. No. 5,457,183, which is a continuation-in-part of application No. 07/822,964, Jan. 21, 1992, Pat. No. 5,252,720, said application No. 08/795,393, is a continuation-in-part of application No. 08/452,261, May 26, 1995, abandoned, which is a continuation of application No. PCT/US94/06284, Jun. 9, 1994, which is a continuation-in-part of application No. 08/227,370, Apr. 14, 1994, Pat. No. 5,559,207, which is a continuation-in-part of application No. 08/075,123, Jun. 9, 1993, abandoned, which is a continuation-in-part of application No. 07/822,964, Jan. 21, 1992, Pat. No. 5,252,720.

[51] Int. Cl.$^7$ ................................................ C07D 487/22

[52] U.S. Cl. .................................... 530/391.7; 530/391.3; 530/391.5; 530/345; 530/405; 534/11; 534/13; 534/15; 534/16; 536/17.1; 536/17.3; 536/17.4; 540/145; 540/465; 540/472

[58] Field of Search ................................... 540/145, 465, 540/472; 536/17.1, 17.3, 17.4; 534/11, 13, 15, 16; 530/391.3, 391.5, 391.7, 345, 405

[56] References Cited

U.S. PATENT DOCUMENTS

| | | | |
|---|---|---|---|
| 5,457,183 | 10/1995 | Sessler et al. | 534/11 |
| 5,504,205 | 4/1996 | Sessler et al. | 540/474 |
| 5,583,220 | 12/1996 | Sessler et al. | 540/472 |
| 5,587,371 | 12/1996 | Sessler et al. | 514/185 |
| 5,599,923 | 2/1997 | Sessler et al. | 540/145 |
| 5,599,928 | 2/1997 | Hemmi et al. | 540/474 |

FOREIGN PATENT DOCUMENTS

WO 9746262  1/1998  WIPO .

*Primary Examiner*—Richard L. Raymond
*Attorney, Agent, or Firm*—David A. Lowin

[57] ABSTRACT

The invention relates to the field of radiation sensitizers and the use of texaphyrins for radiation sensitization and other conditions for which X-ray radiation has proven to be therapeutic.

17 Claims, 17 Drawing Sheets

CONJUGATES OF TEXAPHYRINS

This application is a continuation application of copending application Ser. No. 08/795,393, filed Feb. 4, 1997, now U.S. Pat. No. 5,888,997, which is a continuation-in-part of application Ser. No. 08/437,968, filed May 10, 1995, now U.S. Pat. No. 5,622,946, which is a continuation application of International application PCT/US94/11491, filed on Oct. 12, 1994 and designating the United States of America, which is a continuation-in-part of application Ser. No. 08/135,118, filed Oct. 12, 1993, now U.S. Pat. No. 5,457,183, which is a continuation-in-part of application Ser. No. 07/822,964, filed Jan. 21, 1992, now U.S. Pat. No. 5,252,720; and, said application Ser. No. 08/795,393 is also a continuation-in-art of application Ser. No. 08/452,261, filed May 26, 1995, now abandoned, which is a continuation application of International application PCT/US94/06284, filed Jun. 9, 1994 and designating the United States of America, which is a continuation-in-part of application Ser. No. 08/227,370, filed Apr. 14, 1994, now U.S. Pat. No. 5,559,207, which is a continuation-in-part of application Ser. No. 08/075,123, filed Jun. 9, 1993, now abandoned, which is a continuation-in-part of application Ser. No. 07/822,964, filed Jan. 21, 1992, now U.S. Pat. No. 5,252,720; the entire disclosures of which are incorporated herein by reference.

FIELD OF THE INVENTION

The present invention relates to the field of radiation sensitizers and the use of texaphyrins for radiation sensitization and other conditions for which X-ray radiation has proven to be therapeutic.

BACKGROUND OF THE INVENTION

A radiation sensitizer is an agent used to enhance the effect of radiation therapy. In delivering potentially curative doses of radiation, it is necessary to balance the need for local tumor control with the potential for damage to surrounding normal tissues by the delivered dose of radiation (Bush et al., 1978). It is therefore desirable to use the lowest radiation dose consistent with local control. One way to achieve this would be to utilize a radiation sensitizing agent to enhance cytotoxicity of delivered radiation to the tumor.

Radiation causes cell death by damaging critical targets within the cell, most commonly chromosomal DNA (Hendrickson and Withers, 1991). Radiation therapy relies on two types of ionizing radiation: (1) directly ionizing subatomic particle radiation, such as alpha particles and beta particles (electrons), neutrons, protons, mesons, heavy charged ions, etc., and (2) indirectly ionizing electromagnetic radiation, which exists as a family of waves of varying frequency including high frequency x-rays or gamma rays. However, of the two, electromagnetic radiation is more commonly used in radiation therapy today. In tissue, electromagnetic radiation in the form of x-rays or gamma rays can interact with molecules (especially water) causing the ejection of high-energy electrons. The electrons can break the sugar phosphate bonds in DNA directly (direct action) or the process of electron ejection can ultimately produce free (uncharged) radicals that can also break the chemical (sugar-phosphate) bonds in DNA (indirect action). The damage caused through the indirect mechanism is more significant (Hendrickson and Withers, 1991; Mulcahy et al., 1993; Rubin and Siemann, 1993; Chapman et al., 1974). These damaging effects are mediated by the radiation products of water as shown:

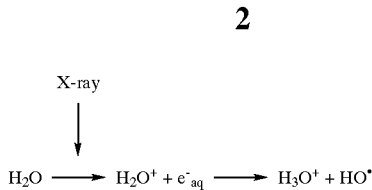

Radiation damage is produced primarily by the hydroxyl radical, HO•, an oxidizing radical. This radical is extremely reactive and short lived. It causes damage primarily in the vicinity in which it is generated (±4 nm). If it comes into contact with a hydrated electron ($e^-_{aq}$), it is deactivated by conversion to a hydroxide ion ($OH^-$). Hydrated electrons are strong reducing species and highly energetic. They are very mobile by comparison to the hydroxyl radical, can travel distances quickly, and through direct action can damage DNA. However, as mentioned above, they also deactivate hydroxyl radicals readily. Agents with strong electron affinity, by virtue of "soaking up" solvated electrons, prevent them from neutralizing hydroxyl radicals and thereby allow hydroxyl radicals to exert their effect (Adams and Dewey, 1963). Oxygen and other compounds with strong electron affinity would thus be expected to act as radiation sensitizers.

The biological responses to radiation-induced cell injury may be modulated by various endogenous and exogenous compounds, and failure of radiation therapy to achieve local cure is multifactorial. For instance, sulfhydryl compounds, including cysteine, dithiothreitol, and cysteamine have been shown to protect living cells against the lethal effects of ionizing radiation by acting as reducing agents (Rubin and Siemann, 1993) and facilitating the recombination of the ion pairs. It also has been observed that depletion of cellular sulfhydryl compounds can result in radiosensitization.

One of the major factors mediating failure of radiation therapy, or radioresistance, is hypoxia. Hypoxic cells in solid tumors have been observed to be 2.5–3 times more resistant to the damaging effect of ionizing radiation (Tannock, 1972; Watson et al., 1978; both cited in Brown, 1984). Local cure/control rates of a tumor can be increased with an effective increase in the radiation dose; however, such an increase would damage adjacent, fully-oxygenated normal tissues to a greater degree than the tumor cells (Shenoy and Singh, 1992). Specific modification of tumor radiosensitivity has been pursued through alteration of the tumor oxygenation state achieved by fractionation of the radiation dose and by the attempted use of chemical radiation sensitizers (Wang, 1988; Shenoy and Singh, 1992).

Fractionation results in reduced radiation effects in normal tissue as compared with a single acute dose due to cell repopulation and repair of sublethal damage between dose fractions. In malignant tumor tissues, radiosensitive oxygenated cells are destroyed with a subsequent reduction in tumor size. Subsequently, radioresistant hypoxic cells distant from functional vasculature become reoxygenated and therefore more radiosensitive. Reassortment of cells within the cell cycle also occurs and renders the cancer cells more radiosensitive. This differential response between tumor and normal cells may allow dose fractionation to be more tumoricidal than an equal single radiation dose.

Various types of electron-affinic reagents are known to promote radiosensitization of cells with diminished oxygen supply (Shenoy and Singh, 1992). However, few of these show activity at non-toxic doses in vivo. For instance, clinical trials with one of the better known agents, misonidazole, demonstrated that it is highly effective against a number of animal and human tumors (Thomlinson et al., 1976; Ash et al., 1979; Denekamp et al., 1980; all cited in Brown, 1984). However, the neurological side-effects severely limit its clinical usefulness (Kallman, 1972; Dische et al., 1977; Urtasun et al., 1978; Waserman et al., 1979; all cited in Brown, 1984; and Dische et al., 1979). Approaches aimed at improving the therapeutic index of nitroimidazoles have included lowering the lipophilicity so as to restrict nervous tissue penetration and toxicity, and accelerating renal clearance (Beard et al., 1993). Clinical trials with these second-generation analogs of misonidazole have been reported or are on-going (Roberts et al., 1984; Coleman et al., 1984; Saunders et al., 1984; Coleman et al., 1986; Horwich et al., 1986; Newman et: al., 1986; Dische et al., 1986.; Coleman et al., 1987; Newman et al., 1988; Workman et al., 1989). However, the approaches have yet to produce highly effective hypoxic cell sensitizers.

Halogenated pyrimidines also have been studied as radiation sensitizers. These agents modify the radiosensitivity of cells through structural alteration of the DNA, making the DNA more susceptible to radiation inactivation. However, the drugs must be present in the cells for extended periods since the degree of radiosensitization is directly related to the degree of thymidine substitution. In addition, the agents may undergo rapid hepatic degradation and dehalogenation (Shenoy and Singh, 1992). The main limiting factor from prolonged use of halogenated pyriinidines has become bone marrow toxicity (Kinsella et al., 1984a; Kinsella et al., 1984b; Kinsella et al., 1985; cited in Shenoy and Singh, 1992).

Hypoxic cell sensitizers fal within the broad category of chemical modifiers of cancer treatment. Chemical modifiers are usually not cytotoxic by themselves but modify or enhance the tissue response to standard radiation therapy. The ultimate utility of a radiotherapy or chemotherapy modifier depends upon its ability to alter the therapeutic index.

Texaphyrins have been described in U.S. Pat. Nos. 4,935, 498; 5,162,509; 5,252,720; 5292,414; 5,272,143; 5,256,399; 5,457,183; 5,559,207; 5,569,759; and 5,599,923; and PCT/US94/06284; all of which are incorporated by reference herein. The photophysical properties of various texaphyrins are reported in U.S. Pat. No. 5,252,720, incorporated by reference herein, and include strong low energy optical absorptions in the 690–880 nm spectral range, a high triplet quantum yield and efficient production of singlet oxygen. U.S. Pat. No. 5,252,720 also describes photosensitized inactivation of enveloped viruses and magnetic resonance imaging (MRI) of atheroma, liver, kidney and tumor using various substituted texaphyrin metal complexes. Altering the polarity and electrical charges of side groups of these macrocycles alters the degree, rate, and site(s) of binding to free enveloped viruses such as HIV-1 and to virally-infected peripheral mononuclear cells, thus modulating photosensitizer take-up and photosensitization of leukemia or lymphoma cells contaminating bone-marrow. Powerful techniques include the use of these texaphyrins in magnetic resonance imaging followed by photodynamic tumor therapy in the treatment of atheroma, and benign and malignant tumors.

The present invention provides texaphyrins for radiation sensitization. Texaphyrins enhance radiation damage and overcome many of the drawbacks of prior art radiation sensitizers.

SUMMARY OF THE INVENTION

The present invention provinces texaphyrins as radiation sensitizers. The present invention further provides a method of radiation therapy for a host harboring a neoplasm or atheroma including the steps of: i) administering to the host a texaphyrin, and ii) administering ionizing radiation to the texaphyrin in proximity to the neoplasm or atheroma. Texaphyrins are demonstrated herein to have radiation sensitization properties; they enhance cytotoxicity from ionizing radiation in the vicinity of the texaphyrin as compared to control experiments. Ionizing radiation includes, but is not limited to, x-rays, internal and external gamma emitting radioisotopes, and ionizing particles.

A texaphyrin is an aromatic pentadentate macrocyclic "expanded porphyrin." Texaphyrins, water-soluble texaphyrins, and methods of preparation are known in the art and are disclosed in the U.S. patents and patent applications previously incorporated by reference herein. Possibly due to its inherent lipophilicity, texaphyrin exhibits greater biolocalization in neoplastic tissue and atheroma relative to non-neoplastic tissue and non-atheromatous plaque. A neoplasm nay be a benign or a malignant tumor.

The above-described method may include the further step of determining localization sites in the host by reference to a detectable texaphyrin. "By reference to a detectable texaphyrin" as used herein means that the location may be found by localization means such as fluorescent spectroscopy, especially when the texaphyrin is non-metallated or is complexed with a diamagnetic metal; magnetic resonance imaging when the texaphyrin contains a metal that is paramagnetic; gamma camera body scanning when the metal is gamma emitting; or by using diagnostic x-rays, especially mono- or polychromatic x-rays with energy around the K electrons of metals bound to texaphyrin. Gamma emitting metals for radioimmunodiagnostics are described in U.S. Pat. No. 5,252,720, incorporated by reference herein. A preferred gamma emitting metal is $^{111}$In(III).

In each of these methods, the texaphyrin may be complexed with a metal, although the metal is not central to the radiosensitization properties of the texaphyrins. The metal can be important to the stability of the texaphyrin complex. The ionizing radiation is from an external source unless the metal is a radioactive metal. In that case, the ionizing radiation is from the radioactive metal and could be in combination with radiation from an external source.

A further embodiment of the present invention is the use of texaphyrins for a combined method of radiation sensitization and photodynamic therapy in the treatment of a neoplasm or atheroma. This method comprises the administration of a photosensitive texaphyrin and delivering ionizing radiation and light in proximity to the neoplasm or atheroma. The photosensitive texaphyrin is a metal-free texaphyrin or a texaphyrin-diamagnetic metal complex. Alternatively, a first texaphyrin may be administered that is detectable so that localization may be accomplished by reference to the detectable texaphyrin. A second, photosensitive texaphyrin may be administered with the first or afterwards so that both radiation sensitization and photodynamic therapy may be carried out. The method comprises the steps of i) administering to the host as a first agent a detectable texaphyrin, ii) determining localization sites in the host by reference to the detectable texaphyrin, iii) administering to the host as a second agent a photosensitive texaphyrin, and iv) administering ionizing radiation and photoirradiation in proximity to the neoplasm or atheroma. The second agent has essentially identical biolocalization property as the first agent and exhibits the ability to generate oxygen upon exposure to light. The photodynamic effect may be derived from anaerobic electron transfer processes or from aerobic, oxygen-based processes. Cytotoxic oxygen products may be singlet oxygen, hydroxyl radicals, superoxide, or hydroperoxyl radicals. The photosensitive texaphyrin may be a diamagnetic metal complex or a metal-free species. Presently preferred diamagnetic metal texaphyrin complexes are the Lu(III), La(III) or In(III) complex of B2T2 (see U.S. Pat. No. 5,252,720, incorporated herein by reference) or of T2BET (see Example 1, this application).

Texaphyrin metal complexes possess inherent biolocalization specificity as described in the '720 patent, localizing in lipid rich regions such as, for example, liver, kidney, tumor and atheroma. "Exhibiting greater biolocalization" in neoplaistic tissue and atheroma as compared to non-neopliistic tissue and non-atheromatous plaque means having ain inherently greater affinity for neoplastic tissue and atheroma relative to non-neoplastic tissue and non-atheromatous plaque.

"Essentially identical biolocalization property" means the second agent is a texaphyrin derivative having about the same selective targeting characteristics in tissue as demonstrated by the first agent. The first agent and the second agent may be the same texaphyrin. Importantly, hydroxylated texaphyrins have a lipid-water distribution coefficient that is optimal for localization to lipophilic regions, yet sufficiently water-soluble to allow ease of handling.

The texaphyrin may be chosen from those of structure A or B:

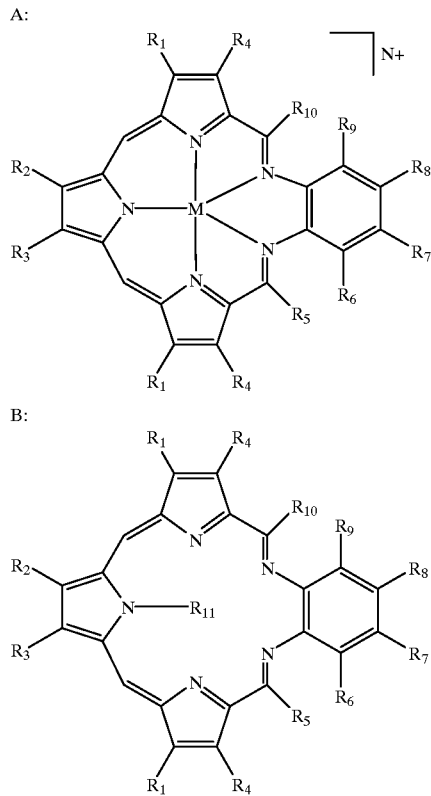

wherein M is H, a divalent metal cation or a trivalent metal cation. A preferred divalent metal cation is selected from the group consisting of Ca(II), Mn(II), Co(II), Ni(II), Zn(II), Cd(II), Hg(II), Fe(II), Sm(II) and $UO_2$(II). A preferred trivalent metal cation is selected from the group consisting of Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

In this texaphyrin structure, $R_1$–$R_4$ and $R_6$–$R_7$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyamidealkyl, a biomolecule a site-directing molecule, a catalytic group, or a couple to a biomolecule, to a site-directing molecule or to a catalytic group. $R_5$ and $R_{10}$ are independently hydrogen, alkyl, aryl, hydroxyalkyl, oxyalkyl, oxyhyroxalkyl, aminoalkyl, oxyaminoalkyl, carboxyalkyl, carboxyamidealkyl, or a couple to a biomolecule, to a site-directing molecule or to a catalytic group; and $R_{11}$ is alkyl, alkenyl, oxyalkyl or hydroxyalkyl having up to about 3 carbon atoms and having rotational flexibility around a first-bound carbon atom. In the above described texaphyrin; where $R_6$ and $R_9$ are other than hydrogen, then $R_5$ and $R_{10}$ are hydrogen or methyl and where $R_5$ and $R_{10}$ are other than hydrogen, then $R_6$ and $R_9$ are hydrogen, hydroxyl, or halide other than iodide. N is 0, 1 or 2.

In the above-described texaphyrins, the halide other than iodide may be fluoride, chloride or bromide. The alkyl, aryl, hydroxyalkyl, oxyalkyl, oxyhydroxyalkyl, saccharide, carboxyalkyl, carboxyamidealkyl, or site-directing molecule is covalently bonded to the texaphyrin via a carbon—carbon or a carbon-oxygen bond. The aryl may be a phenyl substituent or a phenyl having a nitro, carboxy, sulfonic acid, hydroxy, oxyalkyl or halide other than iodide substituent. In this case, the substituent on the phenyl group may be added in a synthetic step after the condensation step which forms the macrocycle.

In one embodiment of the present invention, the texaphyrin is coupled to site-directing molecules to form conjugates for targeted in vivo delivery. "Specificity for targeted sites" means that upon contacting the texaphyrin conjugate with the targeted site, for example, under physiological conditions of ionic strength, temperature, pH and the like, specific binding will occur. The interaction may occur clue to specific electrostatic, hydrophobic, entropic or other interaction of certain residues of the conjugate with specific residues of the target to form a stable complex under conditions effective to promote the interaction.

Exemplary site-directing molecules contemplated in the present invention include but are not limited to: oligodeoxyribonucleotides, oligoribonucleotide analogs; polyamides including peptides having affinity for a biological receptor and proteins such as antibodies, low density lipoproteins, the APO protein of lipoprotein; steroids and steroid derivatives; hormones such as estradiol, or histamine; hormone mimics such as morphine; and further macrocycles such as sapphyrins and rubyrins. An oligonucleotide may be derivatized at the base, the sugar, the ends of the chain, or at the phosphate groups of the backbone to promote in vivo stability. Modification of the phosphate groups is preferred in one embodiment of the invention since phosphate linkages are sensitive to nuclease activity. Preferred derivatives are methylphosphonates, phosphotriesters, phosphorothioates, and phosphoramidates and the like. Additionally, phosphate linkages may be completely substituted with non-phosphate linkages such as amide linkages. Appendages to the ends of the oligonucleotide chain also provide exonuclease resistance. Sugar modifications may include alkyl groups attached to an oxygen of a ribose moiety in a ribonucleotide. In particular, the alkyl group is preferably a methyl group and the methyl group is attached to the 2' oxygen of the ribose. Other alkyl groups may be ethyl or propyl. It is understood that the terms inucleotidel and "oligonucleotide", as used herein, refer to both naturally-occurring and synthetic nucleotides, poly- and oligonucleotides and to analogs and derivatives thereof.

The term "texaphyrin-oligonucleotide conjugate" means that an oligonucleotide is attached to the texaphyrin in a 5' or 3' linkage or both types of linkages to allow the texaphyrin to be an internal residue in the conjugate. The oligonucleotide or other site-directing molecule may be attached either directly to the texaphyrin via a linker, or a couple of variable length. During treatment, for example, the texaphyrin portion of a texaphyrin metal complex-oligonucleotide conjugate is envisioned as being placed in the vicinity of the targeted tissue upon binding of the oligonucleotide to its complementary DNA.

A couple may be described as a linker, i.e., the covalent product formed by reaction of a reactive group designed to attach covalently another molecule at a distance from the texaphyrin macrocycle. Exemplary linkers or couples are amides, amine, thioether, ether, or phosphate covalent bonds as described in the examples for attachment of oligonucleotides. In most preferred embodiments, oligonucleotides and other site-directing molecules are covalently bonded to the texaphyrin via a carbon-nitrogen, carbon-sulfur, or a carbon-oxygen bond. The oligonucleotide, the antibody, the hormone or the sapphyrin may have binding specificity for localization to a treatment site and the biological receptor may be localized to a treatment site.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

The term "catalytic group", as used herein, means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated in the present invention include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or most preferably 2–7, and the like, derivatives thereof and texaphyrin metal complexes. The term "appended to the texaphyrin metal complex-conjugate" means that the catalytic groups are attached either directly to the texaphyrin metal complex via a linker or couple of variable length, or attached to the ligand portion of a texaphyrin complex-ligand conjugate.

While the above structures A and B are presently preferred, the invention is not limited thereto and any texaphyrin or texaphyrin metal complex may be used in the radiation sensitization methods of the present invention.

The method of radiation therapy using texaphyrins provided herein incorporates a number of strategies to optimize specificity of treatment. The first is the inherent biolocalization of texaphyrins to lipid rich tissue, the second is the ability to conjugate site-directing molecules to the periphery of the texaphyrin and the third is the ability to position radiation to a particular site. For example, a complementary oligonucleotide is designed to base pair with the is targeted substrate and the positioning of incident radiation, either by manual or mechanical means, would be particularly advantageous when cytotoxicity is to be effected at a particular biological locus, such as, for instance, a deep-seated tumor site. In this instance, photodynamic therapy may be advantageously combined with radiation therapy for treatment. The fact that the texaphyrins absorb light at wavelengths where bodily tissues are relatively transparent (700–900 nm) is particularly advantageous. This procedure allows for the effective implementation of radiation- and light-based oligonucleotide strategies at loci deep within the body with relatively little radiation damage or photosensitization of other tissues where the texaphyrins or the texaphyrin conjugates are not localized.

In the above-described texaphyrin structure A, N will typically be an integer less than or equal to 2. In the context of the basic macrocycle with a divalent or trivalent metal cation, N is 1 or 2; however, one skilled in the art in light of the present disclosure would realize that the value of N would be altered due to charges present on substituents $R_1$–$R_{10}$ and charges present on the covalently bound site-directing molecule, for example, charges of the phosphate groups on an oligonucleotide.

Alkyl means an alkyl group, straight or branched chain, of 1 to 10 carbon atoms. Alkenyl means an alkenyl group, straight or branched chain, of 1 to 10 carbon atoms and having one or two double bonds. Hydroxyalkyl means an alkyl group having from 1 to 20 hydroxyl groups attached. Alkoxy means an alkyl group attached to an oxygen. Hydroxyalkoxy means an alkyl group having ether linkages, and hydroxyl or substituted hydroxyl groups or the like. Saccharide includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol. Aminoalkyl means alkyl having an amine group. Oxyaminoalkyl means an alkyl group having an ether linkage and having an amine group. Carboxyamidealkyl means an alkyl group with secondary or tertiary amide linkages or the like. Carboxyalkyl means an alkyl group having one or more carboxyl groups, or one or more ester linkages.

For the above-described texaphyrin structures, hydroxyalkoxy may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$. The hydroxyalkoxy or saccharide may be $CH_nH_{((2n+1)-q)}O_yR^a_q$, $OC_nH_{((2n+1)-q)}O_yR^a_q$ or $(CH_2)_n$ $CO_2R^a$ where n is a positive integer from 1 to 10, y is zero or a positive integer less than $((2n+1)-q)$, q is zero or a positive integer less than or equal to $2n+1$, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_n$ $CONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directing molecule. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than $((2n+1)-q)$, q is zero or a positive integer less than or equal to $2n+1$, and $R^c$ is $(CH_2)_nCO_2R^d$, $(CH_2)_nCONHR^d$, $(CH_2)_nCON(R^d)_2$ or a site-directing molecule. In this case, n is a positive integer from 1 to 10, $R^d$ is independently H, alkyl, hydroxyalkyl, saccharide, $C_{(m-w)}$ $H_{((2m+1)-2w)}O_wO_z$, $O_2CC_{(m-w)}H_{((2m+1)-2w)O_wO_z}$ or $N(R)$ $OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide. In a preferred embodiment, $R^c$ is an oligonucleotide.

A presently preferred embodiment of the present invention is a method of radiatin therapy for a host harboring a neoplasm or atheroma comprising the steps of i) administering to the host a pharmaceutically effective amount of the Gd complex of a texaphyrin, and ii) administering ionizing radiation to the texaphyrin in proximity to the neoplasm or atheroma. A more preferred embodiment of the invention is the above method where the texaphyrin is the Gd complex of T2B2, 4,5-diethyl-10,23-dimethyl-9,24-bis(3-hydroxypropyl)-16,17-(3-hydroxypropyloxy)-13,20,25,26,27-pentaazapentacyclo[20.2.1.1$^{3,6}$.1$^{8,11}$.0$^{14,19}$]heptacosa-1,3,5,7,9,11(27),12,14(19),15,17,20,22(25),23-tridecaene, or the Gd complex of T2BET, 4,5-diethyl-10,23-dimethyl-9,24-bis(3-hydroxypropyl)-16,17-bis[2-[2-(2-methoxyethoxy) ethoxy]ethoxy]-pentaazapentacyclo-[20.2.1.1$^{3,6}$.1$^{8,11}$.0$^{14,19}$]heptacosa-1,3,5,7,9,11(27),12,-14,16,18,20,22(25),23-tridecaene. A particularly preferred embodiment is where the texaphyrin is the Gd complex of T2BET.

In presently preferred texapliyrins, $R_1$ is hydroxyalkyl and $R_2$, $R_3$ and $R_4$ are alkyl. Alternatively, $R_3$ may be a site-directed molecule or a couple to a site-directed molecule, preferably an oligonucleotide or a couple to an oligonucleotide. In a further preferred texaphyrin, $R_1$ is $(CH_2)_2CH_2OH$, $R_2$ and $R_3$ are $CH_2CH_3$, $R_4$ is $CH_3$ and $R_7$ and $R_8$ are $OCH_2CH_2CH_2OH$. Alternatively, $R_8$ is a site-directed molecule or a couple thereto, preferably an oligonucleotide or a couple thereto, more preferably $O(CH_2)_n CO$-oligonucleotide where n is 1–7 and preferably 1–3; and $R_7$ is H. In a further presently preferred embodiment, $R_1$ is $(CH_2)_2CH_2OH$, $R_2$ and $R_3$ are $CH_2CH_3$, $R_4$ is $CH_3$, $R_7$ and $R_8$ are $O(CH_2CH_2O)_2CH_2CH_2OCH_3$, alternatively, $R_8$ is a site-directed molecule or a couple thereto, preferably an oligonucleotide or a couple thereto, more preferably $O(CH_2)_n$ CO-oligonucleotide where n is 1–7 and preferably 1–3. In other presently preferred embodiments, $R_1$–$R_{10}$ are as in Table 1 for texaphyrins A1–A38.

Texaphyrins of structure B having a substituent on a pyrrole nitrogen are provided as new compositions of matter. Table 2 of Example 2 presents a summary of substituents contemplated for this derivatized texaphyrin. The pyrrole nitrogen substituent ($R_{11}$) may be alkyl, alkenyl, hydroxyalkyl, or alkoxy group having up to about 3 carbon atoms; with the provision that the substituent has rotational flexibility after the first-bound carbon to allow the rest of the group to be positioned outside the plane of the texaphyrin. Thus, a preferred alkenyl is $CH_2CH=CH_2$. The pyrrole nitrogen substituent is most preferably a methyl group.

A further embodiment of the present invention is a method for synthesizing a texaphyrin having a substituent ($R_{11}$) on a pyrrole nitrogen. The method comprises the steps of i) mixing, in an organic solvent, a nonaromatic texaphyrin having a substituent on a pyrrole nitrogen, a Brønsted base and an oxidant; and ii) stirring at ambient temperature or heating the mixture at reflux for at least two hours. The nonaromatic texaphyrin is produced by condensation of a tripyrrane aldehyde or ketone having structure I; and a substituted ortho-phenylenediamine having structure II:

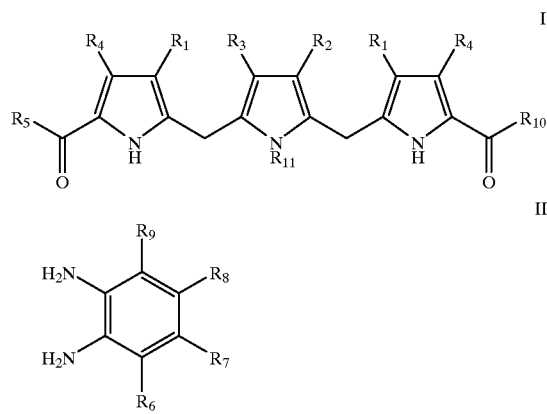

$R_1$–$R_4$ and $R_6$–$R_9$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyamidealkyl, a site-directing molecule, a catalytic group, or a couple to a site-directing molecule or to a catalytic group. $R_5$ and $R_{10}$ are independently hydrogen, alkyl, aryl, hydroxyalkyl, oxyalkyl, oxyhyroxyalkyl, aminoalkyl, oxyaminoalkyl, carboxyalkyl, carboxyamidealkyl, or a couple to a site-directing molecule or to a catalytic group; and $R_{11}$, is alkyl, alkenyl, oxyalkyl or hydroxyalkyl having up to about 3 carbon atoms and having rotational flexibility around a first-bound carbon atom.

In a preferred method of synthesis, $R_{11}$ is methyl, the Brønsted base is triethylamine or N,N,N',N'-tetramethyl-1,8-diaminonaphthalene ("proton sponge"), the oxidant is air and the air is saturating the organic solvent, or the oxidant may be oxygen, platinum oxide, o-chloronyl or 2,3-dichloro-5,6-dicyano-1,4-benzoquinone. The stirring or heating at reflux step may comprise stirring or heating at reflux the mixture for at least 2 hours and up to about 24 hours, and the organic solvent may comprise methanol, methanol and chloroform, or methanol and benzene, or methanol and dimethylformamide.

The pharmaceutical preparations of the present invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a texaphyrin of the present invention and the pharmaceutically acceptable carriers are then easily administered in a variety of dosage forms such as injectable solutions.

For parenteral administration, solutions of the texaphyrin in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A shows the synthesis of a texaphyrin metal complex 3'-linked-oligonucleotide conjugate. FIG. 3B and FIG. 3C show an approach that results in a 5' linked oligonucleotide conjugate. The circle with a squiggle represents controlled pore silica with a linker group.

FIG. 10A shows cell kill without texaphyrin (●) and in the presence of GdT2B2$^{2+}$ (▲), GdT2BET$^{2+}$ (♦), and LuT2BET$^{2+}$ (■). FIG. 10B shows cell kill in the absence (•) and presence of GdT2BET$^{2+}$ at 10 $\mu$M (■), 20 $\mu$M (♦) and 40 $\mu$M (▲) concentrations.

DETAILED DESCRIPTION OF THE PREFERRED EMBODIMENTS

Figure 1A:
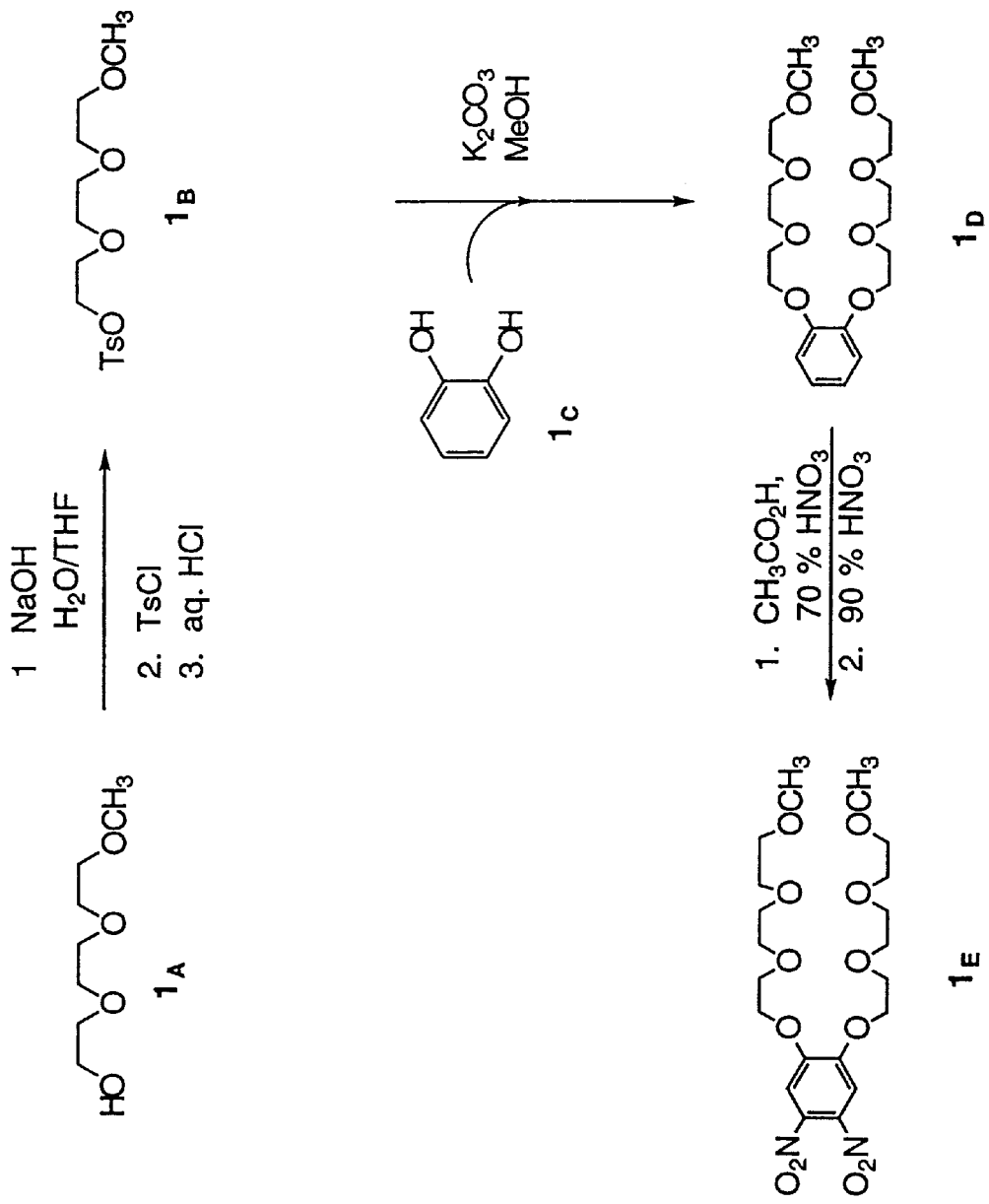
FIG. 1A, FIG. 1B and FIG. 1C show the synthesis of a preferred texaphyrin of the present invention, T2BET$^{2+}$, 4,5-diethyl-10,23-dimethyl-9,24-bis(3-hydroxypropyl)-16,17-bis[2-[2-(2-methoxyethoxy) ethoxy]ethoxy]-13,20,25,26,27-pentaazapentacyclo[20.2.1.1$^{3,6}$.1$^{8,11}$.0$^{14,19}$] heptacosa-1,3,5,7,9,11(27),12,14(19),15,17,20,22(25),23-tridecaene.

The present invention involves the use of texaphyrins for radiosensitization in radiation therapy, and for a two-pronged treatment protocol involving radiation therapy and photodynamic tumor therapy. More particularly, the invention demonstrates enhanced cytotoxicity from radiation and enhanced nucleic acid strand scission in the presence of a texaphyrin. Examples 1–4, 9 and 10 describe the synthesis of preferred texaphyrins and texaphlyrins conjugated to site-directing molecules or to catalytic groups. Examples 5–8 describe the use of texaphyrins for radiosensitization, radiation therapy and radiation therapy with photodynamic tumor therapy.

The synthesis of texaphyrins is described in U.S. Pat. Nos. 4,935,498; 5,162,509; 5,252,720; 5,457,183; 5,530,122; 5,559,207; 5,569,759; and 5,599,923; all of which are incorporated by reference herein. Substituents at the $R_6$–$R_9$ positions on the B (benzene ring) portion of the macrocycle are incorporated into the macrocycle by their attachment to the precursor, ortho-phenylenediarnine in the 3, 4, 5, and 6 positions of the molecule. The introduction of substituents on the T (tripyrrane) portion of the molecule is accomplished by appropriate functionalization of the pyrrole rings, and substituents at the $R_5$ and $R_{10}$ positions are incorporated by appropriate functionalization of the tripyrrane in the 5 positions at a synthetic step prior to condensation with a substituted ortho-phenylenediamine. More preferred functionalizations are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide.

Any texaphyrin or texaphyrin metal complex may be used as a radiation sensitizer. Representative substituents of preferred texaphyrins of structure A for radiation sensitization are listed in Table 1. $R_4$ is preferably methyl for these compounds.

TABLE 1

Representative Substituents for Texaphyrin

| TXP | $R_1$ | $R_2$ | $R_3$ | $R_5$ | $R_6$ | $R_7$ | $R_8$ | $R_9$ | $R_{10}$ |
|---|---|---|---|---|---|---|---|---|---|
| A1 | $CH_2(CH_2)_2OH$ | $CH_2CH_3$ | $CH_2CH_3$ | H | COOH | $O(CH_2)_3OH$ | $O(CH_2)_3OH$ | $O(CH_2)_3OH$ | H |
| A2 | $CH_2(CH_2)_2OH$ | " | " | " | COOH | $O(CH_2CH_2O)_3CH_3$ | $O(CH_2CH_2O)_3CH_3$ | COOH | " |
| A3 | $CH_2(CH_2)_2OH$ | " | " | " | CONHCH—$(CH_2OH)_2$ | $O(CH_2CH_2O)_3CH_3$ | $O(CH_2CH_2O)_3CH_3$ | O-saccharide | " |
| A4 | $CH_2(CH_2)_2OH$ | " | " | " | CONHCH—$(CH_2OH)_2$ | $O(CH_2CH_2O)_3CH_3$ | " | $O(CH_2CH_2O)_3CH_3$ | " |
| A5 | $CH_2(CH_2)_2OH$ | " | " | " | H | $O(CH_2CH_2O)_3CH_3$ | $O(CH_2)_3CON$-linker-oligo | $O(CH_2CH_2O)_3CH_3$ | " |
| A6 | $CH_2(CH_2)_2OH$ | " | " | " | $OCH_3$ | H | $OCH_2CON$-linker-oligo | $OCH_3$ | " |
| A7 | $CH_2(CH_2)_2OH$ | " | " | " | " | " | $OCH_2CO$-poly-L-lysine | " | " |
| A8 | $CH_2(CH_2)_2OH$ | " | " | " | " | " | $OCH_2CO$-estradiol | " | " |
| A9 | $CH_2(CH_2)_2OH$ | " | " | " | " | " | $O(CH_2CH_2O)_3CH_3$ | " | " |
| A10 | $CH_2(CH_2)_2OH$ | " | " | " | " | $O(CH_2CH_2O)_3CH_3$ | " | " | " |
| A11 | $CH_2(CH_2)_2OH$ | " | " | " | " | $O(CH_2CH_2O)_3CH_3$ | $OCH_2CON$-linker-oligo | " | " |
| A12 | $CH_2(CH_2)_2OH$ | " | " | " | " | $O(CH_2CH_2O_3CH_3$ | $OCH_2CO$-estradiol | " | " |
| A13 | $CH_2(CH_2)_2OH$ | " | " | " | $CH_3$ | $O(CH_2CH_2O)_3CH_3$ | $O(CH_2CH_2O)_3CH_3$ | $O(CH_2CH_2O)_3CH_3$ | " |
| A14 | $CH_2(CH_2)_2OH$ | " | " | " | " | $O(CH_2CH_2O_3CH_3$ | $OCH_2CO$-estradiol | $O(CH_2CH_2O)_3CH_3$ | " |

TABLE 1-continued

Representative Substituents for Texaphyrin

| TXP | $R_1$ | $R_2$ | $R_3$ | $R_5$ | $R_6$ | $R_7$ | $R_8$ | $R_9$ | $R_{10}$ |
|---|---|---|---|---|---|---|---|---|---|
| A15 | $CH_2(CH_2)_2OH$ | " | " | " | " | $O(CH_2CH_2O)_3CH_3$ | $O(CH_2CH_2O)_{120}CH_3$ | $OCH_3$ | " |
| A16 | $CH_2(CH_2)_2OH$ | " | " | " | " | H | saccharide | " | " |
| A17 | $CH_2(CH_2)_2OH$ | " | " | $CH_3$ | H | $O(CH_2)_3OH$ | $O(CH_2)_3OH$ | H | $CH_3$ |
| A18 | $CH_2(CH_2)_2OH$ | " | " | " | " | H | $O(CH_2CH_2O)_3CH_3$ | " | " |
| A19 | $CH_2(CH_2)_2OH$ | " | " | " | " | $O(CH_2CH_2O)_3CH_3$ | " | " | " |
| A20 | $CH_2(CH_2)_2OH$ | $CH_2CH_3$ | $CH_2CH_3$ | $CH_3$ | H | H | $OCH_2CON$-linker-oligo | H | $CH_3$ |
| A21 | $CH_2(CH_2)_2OH$ | " | " | " | " | " | $OCH_2CO$-estradiol | " | " |
| A22 | $CH_2(CH_2)_2OH$ | " | " | " | " | " | $OCH_2CON(CH_2CH_2OH)_2$ | " | " |
| A23 | $CH_2(CH_2)_2OH$ | " | " | " | " | $O(CH_2CH_2O)_3CH_3$ | $O(CH_2CH_2O)_{120}CH_3$ | " | " |
| A24 | $CH_2(CH_2)_2OH$ | " | " | " | " | $O(CH_2CH_2O)_3CH_3$ | $OCH_2CON$-linker-oligo | " | " |
| A25 | $CH_2(CH_2)_2OH$ | " | " | " | " | H | $CH_2CON(CH_3)CH_2(CHOH)_4CH_2OH$ | " | " |
| A26 | $CH_2(CH_2)_2OH$ | " | " | " | OH | $O(CH_2CH_2O)_3CH_3$ | $O(CH_2CH_2O)_3CH_3$ | OH | " |
| A27 | $CH_2(CH_2)_2OH$ | " | " | " | F | $O(CH_2CH_2O)_3CH_3$ | " | F | " |
| A28 | $CH_2(CH_2)_2OH$ | " | " | $CH_2(CH_2)_6OH$ | H | $O(CH_2CH_2O)_3CH_3$ | " | H | $CH_2(CH_2)_6OH$ |
| A29 | $CH_2(CH_2)_2OH$ | " | " | H | Br | $O(CH_2CH_2O)_3CH_3$ | " | Br | H |
| A30 | $CH_2(CH_2)_2OH$ | " | " | " | $NO_2$ | $O(CH_2CH_2O)_3CH_3$ | " | $NO_2$ | " |
| A31 | $CH_2(CH_2)_2OH$ | " | " | " | COOH | $O(CH_2CH_2O)_3CH_3$ | " | COOH | " |
| A32 | $CH_2(CH_2)_2OH$ | " | " | " | $CH_3$ | $O(CH_2CH_2O)_3CH_3$ | " | $CH_3$ | " |
| A33 | $CH_2(CH_2)_2OH$ | " | " | $C_6H_5$ | H | $O(CH_2CH_2O)_3CH_3$ | " | H | $C_6H_5$ |
| A34 | $CH_2(CH_2)_2OH$ | COOH | COOH | $CH_2CH_3$ | " | $O(CH_2CH_2O)_3CH_3$ | " | " | $CH_2CH_3$ |
| A35 | $CH_2(CH_2)_2OH$ | $COOCH_2CH_3$ | $COOCH_2CH_3$ | $CH_3$ | " | $O(CH_2CH_2O)_3CH_3$ | " | " | $CH_3$ |
| A36 | $CH_2CH_2CON(CH_2CH_2OH)_2$ | $CH_2CH_3$ | $CH_2CH_3$ | " | " | $O(CH_2CH_2O)_3CH_3$ | " | " | " |
| A37 | $CH_2CH_2ON(CH_3)CH_2$—$(CHOH)_4CH_2OH$ | " | " | " | " | $OCH_3$ | $OCH_3$ | " | " |
| A38 | $CH_2CH_3$ | " | " | $CH_2(CH_2)_6OH$ | " | H | $OCH_2CO_2$-glucosamine | " | $CH_2(CH_2)_6OH$ |

A substituent on the $R_5$ or $R_{10}$ position of the macrocycle may be derivatized either before or after condensation of the macrocycle. Substituents may include an alkyl group having up to 5 carbon atoms or a phenyl group that may be further derivatized with a nitro, carboxyl, sulfonic acid, hydroxyl, halide or alkoxy where the alkyl of the alkoxy may be hydroxyalkyl and the like.

Divalent and trivalent metal complexes of texaphyrins are by convention shown with a formal charge of $N^+$, where N is 1 or 2, respectively. It is understood by those skilled in the art that the complexes described in the present invention may have one or more additional ligands providing charge neutralization and/or is coordinative saturation to the metal ion. Such ligands include chloride, nitrate, acetate, and hydroxide, among others.

The presence of the metal is not important for the radiosensitization properties of texaphyrins; however, the metal contributes stability to the texaphyrin complex. A metal texaphyrin complex with its counterions is considered a neutral complex for purposes of this application; for example, $GdT2B2(OAc)_2$ is a neutral complex. A metal complex of texapliyrin, such as $GdT2B2^{2+}$ has two positive charges. When $GdT2B2^{2+}$ picks up an electron, it becomes a short-lived π-radical cation, $GdT2B2^{+\cdot}$. The cation picks up a proton or rearranges to the texaphyrin radical, $GdT2B2$ (H·), which has significant stability as described in Example 5.

Oxygen is the ultimate electron acceptor in physiological systems. However, texaphyrins have a redox potential below that of oxygen. All reductants will reduce texaphyrin, even superoxide, as can be seen from the following listing of redox potentials:

$e^-_{aq}$=−2.80 V.

Porphyrin=−0.6 to −1.8 V.

Quinone=−0.2 to −1.0 V.

$O^-_2$=−0.18 V.

$GdT2B2^{\cdot-}$=+0.08 V.

Therefore, without being bound by theory, it is believed that gadolinium texaphyrin "soaks up" electrons readily, and prevents their reaction with hydroxyl radicals or other oxidized species. This low redox potential of gadolinium texaphyrin is a property of texaphyrin that enhances the amount of radiation damage incurred at the site of the texaphyrin; in the absence of texaphyrin, hydroxyl radicals and hydrated electrons recombine and little radiation damage occurs, whereas in the presence of texaphyrin, hydroxyl radicals are free to cause damage. Furthermore, the trapping of electrons by texaphyrin prevents the hydrated electrons from interacting with the hydroxyl radical-induced damage site to repair the damage.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Synthesis of Texaphyrin T2BET

The present example provides the synthesis of a preferred texaphyrin, named T2BET, having substituents containing ethoxy groups.

Lutetium(III) acetate hydrate was purchased from Strem Chemicals, Inc. (Newburyport, Mass.) and gadolinium(III) acetate tetrahydrate was from Aesar/Johnson Matthey (Ward Hill, Mass.). The LZY-54 zeolite was purchased from UOP (Des Plaines, Ill.). Acetone, glacial acetic acid, methanol, ethanol, isopropyl alcohol, and n-heptanes were purchased from J. T. Baker (Phillipsburg, N.J.). Triethylamine and Amberlite 904 anion exchange resin were purchased from Aldrich (Milwaukee, Wis.). All chemicals were ACS grade and used without further purification.

Figure 1B:
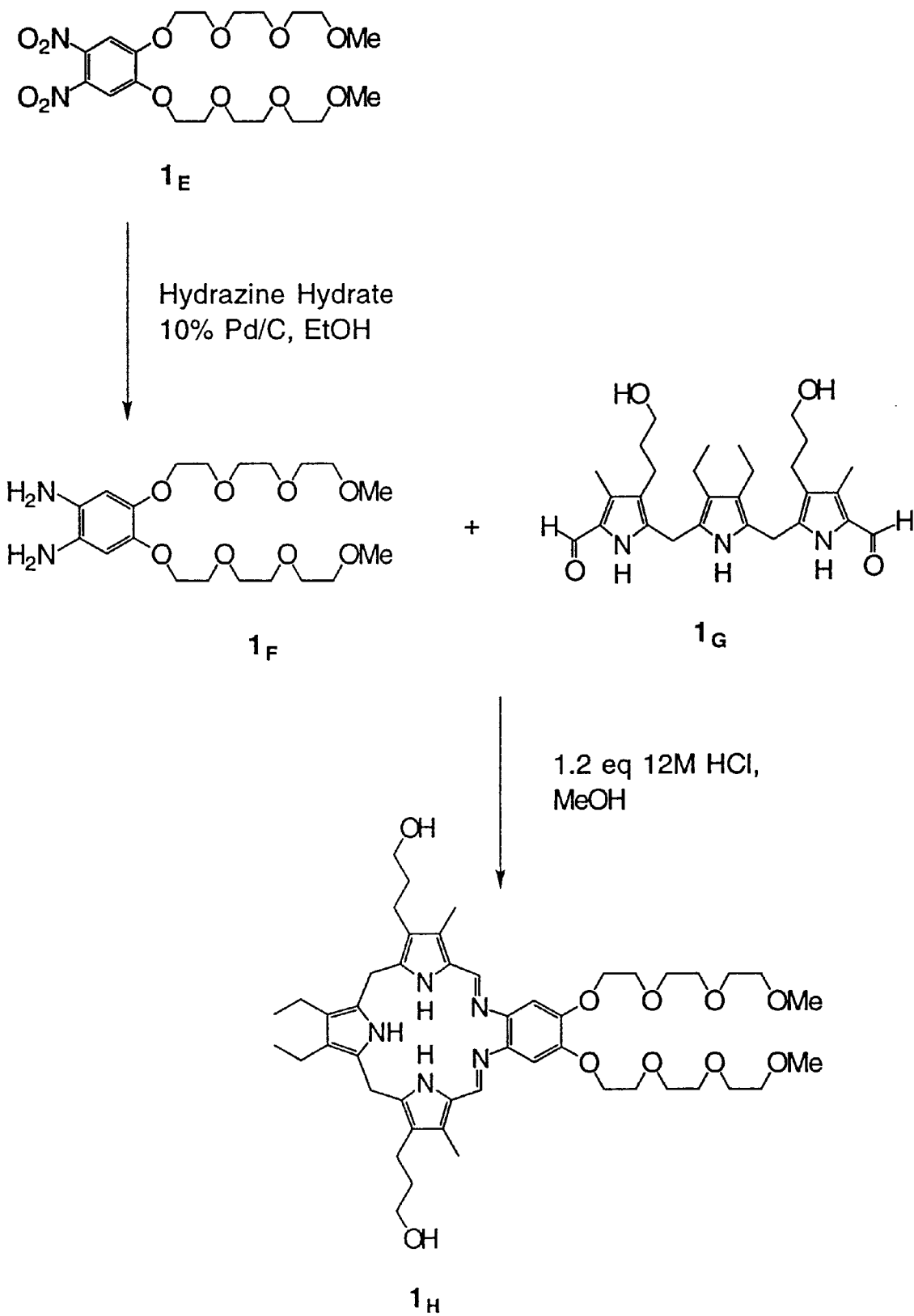
Figure 1C:
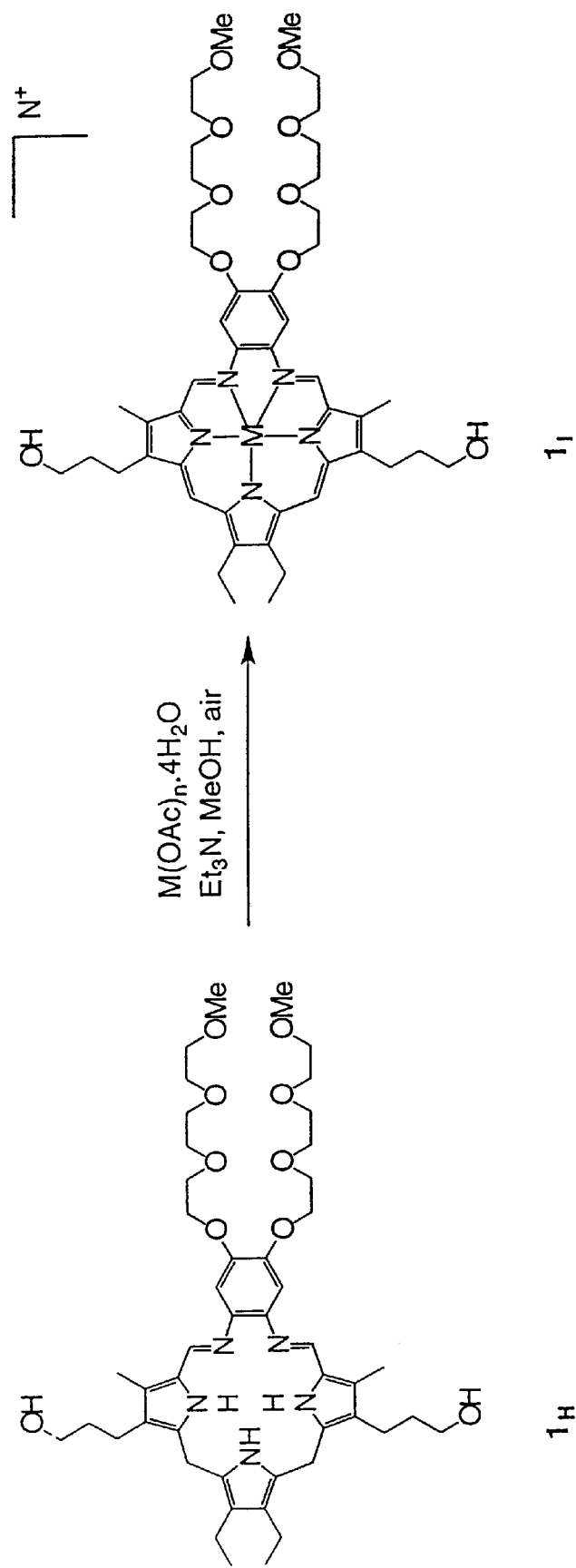

Synthesis of the gadolinium (III) complex of 4,5-diethyl-10,23-dimethyl-9,24-bis(3-hydroxypropyl)-16,17-bis[2-[2-(2-methoxyethoxy)ethoxy]ethoxy]-pentaazapentacyclo [20.2.1.1$^{3,6}$.1$^{8,11}$.0$^{14,19}$]heptacosa-1,3,5,7,9,11(27),12,14, 16,18,20,22(25),23-tridecaene ($1_I$, FIG. 1A, FIG. 1B AND FIG. 1C). The critical intermediate 1,2-bis[2-[2-(2-methoxyethoxy)ethoxy)ethoxy]-4,5-dinitrobenzene, $1_E$ was prepared according to the three-step synthetic process outlined in FIG. 1A.

Synthesis of triethylene glycol monomethyl ether monotosylate, $1_B$: In an oven dried 12 L three-necked round-bottom flask, equipped with a magnetic stir bar and a 1000 mL pressure-equalizing dropping funnel, a solution of NaOH (440.0 g, 11.0 mol) in water (1800 mL) was added, and the mixture was cooled to 0° C. A solution of triethylene glycol monomethyl ether $1_A$ (656.84 g, 4.0 mol) in THF (1000 mL) was added. The clear solution was stirred vigorously at 0° C. for 15 min and a solution of tosyl chloride (915.12, 4.8 mol) in THF (2.0 L) was added dropwise over a 1 h period. The reaction mixture was stirred for an additional 1 h at 0° C., and 10% HCl (5.0 L) was added to quench the reaction (to pH 5–7). The two-phase mixture was transferred in portions to a 4 L separatory funnel, the organic layer removed, and the aqueous layer extracted with t-butylmethyl ether (3×250 mL). The combined organic extracts were washed with brine (2×350 mL), dried (MgSO$_4$), and evaporated under reduced pressure to afford $1_B$, 1217.6 g (95%) as a light colored oil. This material was taken to the next step without further purification.

Synthesis of 1,2-bis[2-[2-(2-methoxyethoxy)ethoxy] ethoxy]-benzene $1_D$. In a dry 5 L round-bottom flask equipped with an overhead stirrer, reflux condenser, and a gas line, K$_2$CO$_3$ (439.47 g, 3.18 mol) and MeOH (1800 mL) were combined under an argon atmosphere. To this well-stirred suspension, catechol $1_C$ (140.24 g, 1.27 mol) was added, and the mixture was heated to reflux. $1_B$ (1012.68 g, 3.18 mol) was then added in one portion. The suspension was stirred at reflux for 24 h, cooled to room temperature, and filtered through Celite. The pad was rinsed with 500 mL of methanol and the combined filtrates were evaporated under reduced pressure. The resulting brown residue was taken up in 10% NaOH (800 mL), and methylene chloride (800 mL) was added with stirring. The mixture was transferred to a 2 L separatory funnel, the organic layer removed and the aqueous layer extracted with methylene chloride (3×350 mL). The organic extracts were combined, washed with brine (350 mL), dried (MgSO$_4$), evaporated under reduced pressure, and the residue dried in vacuo for several hours to yield 485.6 g (95%) of 1,2-bis[2-[2-(2-methoxyethoxy)ethoxy]ethoxy]benzene $1_D$. For $1_D$: bp. 165–220° C., (0.2–0.5 mm Hg); FAB MS, M$^+$: m/e 402; HRMS, M$^+$: 402.2258 (calcd. for C$_{20}$H$_{34}$O$_8$, 402.2253).

Synthesis of 1,2-bis[2-[2-(2-methoxyethoxy)ethoxy] ethoxy]-4,5-dinitrobenzene $1_E$. In an oven dried 1 L round-bottom flask, $1_D$ (104 g, 0.26 mol) and glacial acetic acid (120 mL) were combined and cooled to 5° C. To this well stirred solution, concentrated nitric acid (80 mL) was added dropwise over 15–20 min. The temperature of the mixture was held below 40° C. by cooling and proper regulation of the rate of addition of the acid. After addition the reaction was allowed to stir for an additional 10–15 min and was then cooled to 0° C. Fuming nitric acid (260 mL) was added dropwise over 30 min while the temperature of the solution was held below 30° C. After the addition was complete, the red colored solution was allowed to stir at room temperature until the reaction was complete (ca. 5 h, TLC: 95/5; CH$_2$Cl$_2$/MeOH) and then poured into well stirred ice water (1500 mL). Methylene chloride (400 mL) was added, the two-phase mixture was transferred to a 2 L separatory funnel and the organic layer was removed. The aqueous layer was extracted with CH$_2$Cl$_2$(2×150 mL) and the combined organic extracts were washed with 10% NaOH (2×250 mL) and brine (250 mL), dried (MgSO$_4$), and concentrated under reduced pressure. The resulting orange oil was dissolved in acetone (100 mL), and the solution layered with n-hexanes (500 mL), and stored in the freezer. The resulting precipitate was collected by filtration to yield 101.69 g (80%) of $1_E$ as a yellow solid. For $1_E$: mp 43–45° C.; FAB MS, (M+H)$^+$: m/e 493; HRMS, (M+H)$^+$: 493.2030 (calcd. for C$_{20}$H$_{33}$N$_2$O$_{12}$, 493.2033).

Synthesis of 1,2-diamino-4,5-bis[2-[2-(2-methoxyethoxy)ethoxy]ethoxy]benzene, $1_F$, FIG. 1B. In an oven dried 500 mL round bottom flask, equipped with a Claisen adapter, pressure equalizing dropping funnel, and reflux condenser, 1,2-bis[2-[2-(2-methoxyethoxy)ethoxy] ethoxy]-4,5-dinitrobenzene $1_E$ (20 g, 0.04 mol) was dissolved in absolute ethanol (200 mL). To this clear solution, 10% palladium on carbon (4 g) was added and the dark black suspension was heated to reflux under an argon atmosphere. Hydrazine hydrate (20 mL) in EtOH (20 mL) was added dropwise over 10 min to avoid bumping. The resulting brown suspension was heated at reflux for 1.5 h at which time the reaction mixture was colorless and TLC analysis (95/5; $CH_2Cl_2$/MeOH) displayed a low $R_f$ UV active spot corresponding to the diamine Therefore, the mixture was hot filtered through Celite and the pad rinsed with absolute ethanol (50 mL). The solvent was removed under reduced pressure and the resulting light brown oil was dried in vacuo (in the dark) for 24 h to yield 15.55 g (89%) of 1,2-diamino-bis[2-[2-(2-methoxyethoxy)ethoxy]ethoxy]benzene $1_F$. For $1_F$: FAB MS, $M^+$: m/e 432; HRMS, $M^+$: 432.2471 (calcd. for $C_{20}H_{36}N_2O_8$, 432.2482). This material was taken to the next step without further purification.

Synthesis of 4,5-diethyl-10,23-dimethyl-9,24-bis(3-hydroxypropyl)-16,17-bis[2-[2-(2-methoxyethoxy)ethoxy]ethoxy]-13,20,25,26,27-pentaazapentacyclo[20.2.1.1$^{3,6}$.18, 11.0$^{14,19}$]heptacosa-3,5,8,10,12,14,16,18,20,22,24-undecaene ($1_H$). In an oven dried 1 L round-bottom flask, 2,5-bis[(5-formyl-3-(3-hydroxypropyl)-4-methyl-pyrrol-2-yl)methyl]-3,4-diethylpyrrole $1_G$ (The synthesis of $1_G$ is provided in U.S. Pat. No. 5,252,720, incorporated by reference herein.) (30.94) g, 0.0644 mol) and 4,5-diamino-bis[2-[2-(2-methoxyethoxy)ethoxy]ethoxy]benzene $1_F$ (28.79 g, 0.0644 mol) were combined in absolute methanol (600 mL) under an argon atmosphere. To this well stirred suspension, a mixture of concentrated hydrochloric acid (6.7 mL) in absolute methanol (200 mL) was added in one portion. The mixture was gradually heated to 50° C., at which time the reaction went from a cloudy suspension of starting materials to a dark red homogeneous solution as the reaction proceeded. After 3 h the reaction was judged complete by TLC analysis and UV/visible spectroscopy ($\lambda_{max}$ 369 nm). The reaction mixture was cooled to room temperature, 60 g of activated carbon (DARCO™) was added, and the resulting suspension was stirred for 20 min. The dark suspension was filtered through Celite to remove the carbon, the solvent evaporated to dryness, and the crude $1_H$ dried in vacuo overnight. $1_H$ was recrystallized from isopropyl alcohol/n-heptane to afford 50 g (85%) of a scarlet red solid. For $1_H$:
$^1$H NMR (CD$_3$OD): δ 1.11 (t, 6H, CH$_2$CH$_3$), 1.76 (p, 4H, pyrr-CH$_2$CH$_2$CH$_2$OH), 2.36 (s, 6H, pyrr-CH$_3$), 2.46 (q, 4H, CH$_2$CH$_3$), 2.64 (t, 4H, pyrr-CH$_2$CH$_2$CH$_2$OH), 3.29 [s, 6H, (CH$_2$CH$_2$O)$_3$CH$_3$], 3.31 (t, 4H, pyrr-CH$_2$CH$_2$CH$_2$OH), 3.43–3.85 (m, 20H,CH$_2$CH$_2$OCH$_2$ CH$_2$OCH$_2$ CH$_2$O), 4.10 (s, 4H, (pyrr)$_2$—CH$_2$), 4.22 (t, 4H, PhOCH$_2$CH$_2$O), 7.45 (s, 2H, PhH), 8.36 (s, 2H, HC=N); UV/vis: [(MeOH) $\lambda_{max}$, nm]: 369; FAB MS, [M+H]$^+$: m/e 878.5; HRMS, [M+H]$^+$: m/e 878.5274 (calcd. for [C$_{48}$H$_{72}$N$_5$O$_{10}$]$^+$, 878.5279).

Synthesis of the gadolinium (III) complex of 4,5-diethyl-10,23-dimethyl-9,24-bis(3-hydroxypropyl)-16,17-bis[2-[2-(2-methoxyethoxy)ethoxy]ethoxy]-pentaazapentacyclo [20.2.1.1$^{3,6}$.1$^{8,11}$.0$^{14,19}$]heptcosa-1,3,5,7,9,11(27),12,14,16, 18,20,22(25),23-tridecane $1_I$. $1_I$ was prepared according to the process outlined in FIG. 1C. In a dry 2 L three-necked round-bottom flask, $1_H$ (33.0 g, 0.036 mol) and gadolinium (III) acetate tetrahydrate (15.4 g, 0.038 mol) were combined in methanol (825 mL). To this well stirred red solution, gadolinium(III) acetate tetrahydrate (15.4 g, 0.038 mol) and triethylamine (50 mL) were added and the reaction was heated to reflux. After 1.5 h, air was bubbled (i.e., at reflux) for 4 h into the dark green reaction solution with aid of a gas dispersion tube (flow rate=20 cm$^3$/min). At this point, the reaction mixture was carefully monitored by UV/Visible spectroscopy (i.e., a spectrum is taken every 0.5–1 h, ~1 drop diluted in 4–5 mL MeOH). The reaction was deemed complete by UV/Vis (In MeOH ratio: 342 nm/472 nm=0.22–0.24) after 4 h. The dark green reaction was cooled to room temperature, filtered through Celite into a 2 L round-bottom flask, and the solvent removed under reduced pressure. The dark green solid was suspended in acetone (1 L) and the resulting slurry was stirred for 1 h at room temperature. The suspension was filtered to remove the red/brown impurities (incomplete oxidation products), the solids rinsed with acetone (200 mL), and air dried. The crude complex (35 g) was dissolved in MEOH (600 mL), stirred vigorously for 15 min, filtered through Celite, and transferred to a 2 L Erlenmeyer flask. An additional 300 mL of MeOH and 90 mL water were added to the flask, along with acetic acid washed LZY-54 zeolite (150 g). The suspension was agitated with an overhead mechanical stirrer for approximately 3–4 h. The zeolite extraction is deemed complete with the absence of free Gd(III). [To test for free gadolinium, the crude $1_I$ was spotted heavily onto a reverse phase TLC plate (Whatman KC8F, 1.5×10 cm) and the chromatogram developed using 10% acetic acid in methanol. The green complex moved-up the TLC plate close to the solvent front. Any free gadolinium metal will remain at the origin under these conditions. After developing the chromatogram, the plate was dried and the lower ¼ of the plate stained with an Arsenazo III solution in methanol (4 mg Arsenazo III in 10 mL methanol). A very faint blue spot (indicative of free metal) was observed at the origin against a pink background indicating very little free gadolinium metal.] The zeolite was removed through a Whatman #3 filter paper and the collected solids rinsed with MeOH (200 mL). The dark green filtrate was loaded onto a column of Amberlite IRA-904 anion exchange resin (30 cm length×2.5 cm diameter) and eluted through the resin (ca. 10 mL/min flow rate) into a 2 L round bottom flask with 300 mL 1-butanol. The resin was rinsed with an additional 100 mL of MeOH and the combined eluent evaporated to dryness under reduced pressure. The green shiny solid $1_I$ was dried in vacuo for several hours at 40° C. To a well stirred ethanoic solution (260 mL) of $1_I$ at 55–60° C., n-heptanes (ca. 600 mL) was added dropwise (flow=4 mL/min) from a 1 L pressure-equalizing dropping funnel. During the course of 1.5 h (300 mL addition) the green complex, $1_I$ began to crystallize out of the dark mixture. After complete addition, the green suspension was cooled and stirred for 1 h at room temperature. The suspension was filtered, the solids rinsed with acetone (250 mL), and dried in vacuo for 24 h to afford 26 g (63%). UV/vis: [(MeOH) $\lambda_{max}$, nm]: 316, 350, 415, 473, 739; FAB MS, (M−20Ac)$^+$: m/e 1030; HRMS, (M−20Ac)$^+$: m/e 1027.4036 (calcd. for C$_{48}$H$_{66}^{155}$GdN$_5$O$_{10}$, 1027.4016). Anal. calcd. for [C$_{52}$H$_{72}$GdN$_5$O$_{14}$].0.5H$_2$O: C, 53.96; H, 6.36; N, 6.05, Gd, 13.59. Found: C, 53.73; H, 6:26; N, 5.82; Gd, 13.92.

Synthesis of the Lutetium (III) Complex of $1_H$. The macrocyclic ligand $1_H$ (14 g, 0.0153 mol) was oxidatively metallated using lutetium(III) acetate hydrate (9.75 g, 0.0230 mol) and triethylamine (22 mL) in air-saturated methanol (1500 mL) at reflux. After 3–4 h at reflux, air was bubbled for 40 min into the dark brown/green reaction solution with aid of a gas dispersion tube (flow rate=20 cm$^3$/ml). At this point, reflux continued overnight. After 23 h, air was re-bubbled an additional 40 min to complete the oxidation/metallation. The reaction continued at reflux for 5 h and then it was judged complete by the characteristic UV-visible spectrum. The deep green solution was cooled to room temperature, filtered through a pad of celite, and the solvent removed under reduced pressure. The dark green solid was suspended in acetone (600 mL), stirred for 30 min at room temperature, and then filtered to wash away the red/brown impurities (incomplete oxidation products and excess triethylamine). The crude complex was dissolved into MeOH (300 mL), stirred for ~30 min, and then filtered through celite into a 1 L Erlenmeyer flask. An additional 50 mL of MeOH and 50 ml, of water were added to the flask along with acetic acid washed LZY-54 zeolite (40 g) The resulting mixture was agitated or shaken for 3 h, then filtered to remove the zeolite. The zeolite cake was rinsed with MeOH (100 mL) and the rinse solution added to the filtrate. The filtrate was first concentrated to 150 mL and then loaded onto a column (30 cm length×2.5 cm diameter) of pretreated Amberlite IRA-904 anion exchange resin (resin in the acetate form). The eluent containing the bis-acetate lutetium (III) texaphyrin complex was collected, concentrated to dryness under reduced pressure, and recrystallized from anhydrous methanol/t-butylmethyl ether to afford 11.7 g (63%) of a shiny green solid. For the complex: UV/vis: [(MeOH) $\lambda_{max}$, nm (log $\epsilon$)]: 354,414,474 (5.10), 672, 732; FAB MS, [M–OAc$^-$]$^+$: m/e 1106.4; HRMS, [M–OAc$^-$]$^+$: m/e 1106.4330 (calcd. for $[C_{48}H_{66}LuN_5O_{10}(OAc)]^+$, 1106.4351). Anal. calcd. for $[C_{52}H_{72}LuN_5O_{14}]H_2O$: C, 52.74; H, 6.30; N, 5.91. Found: C, 52.74; H, 6.18; N, 5.84.

EXAMPLE 2

Texaphyrin Derivatized at a Pyrrole Nitrogen

Figure 2:
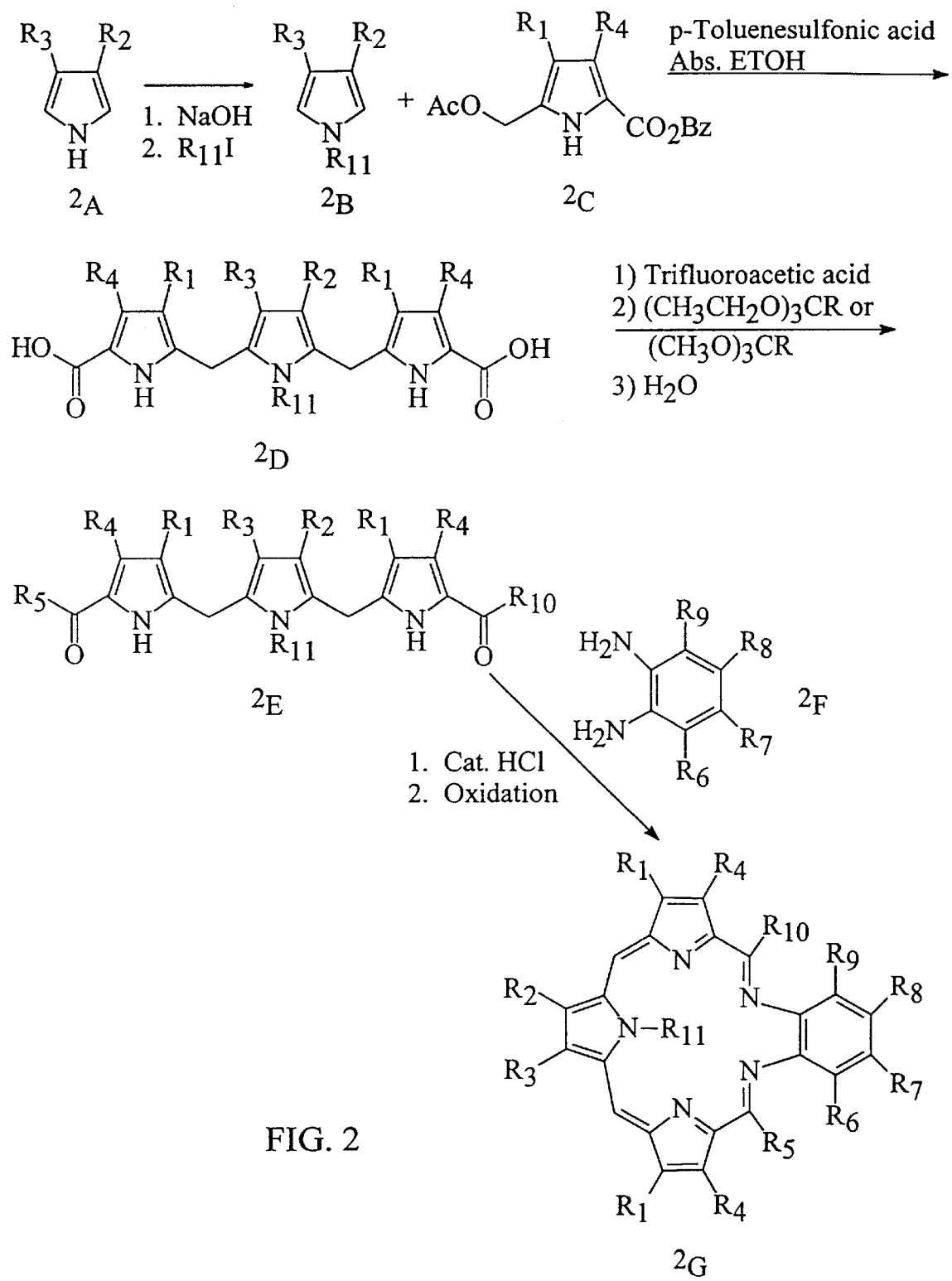
FIG. 2 shows the synthesis of a derivatized texaphyrin having an substituent on a pyrrole nitrogen, 2$_G$.

A further texaphyrin macrocycle is one where a pyrrole nitrogen is derivatized. FIG. 2 shows the synthesis of such an N-substituted texaphyrin where an $R_{11}$ group is attached to the nitrogen of the central pyrrole of the precursor tripyrrole $2_E$. Wang et al., (1977) provides one method. for N-alkylation of pyrrole. The synthesis of texaphyrin compounds having substituents $R_5$, $R_6$, $R_9$ and $R_{10}$ as shown in FIG. 2 is described in U.S. Ser. No. 08/196,964, incorporated by reference herein. The free base macrocycle is particularly useful when fluorescence detection is used as the localization means for radiation sensitization. Optical characteristics of various texaphyrin complexes are described in Sessler et al. (1991), incorporated by reference herein.

Table 2 presents a summary of substituents contemplated for the pyrrole-nitrogen derivatized texaphyrin $2_G$. For this texaphyrin, $R_2$ and $R_3$ are preferably ethyl and $R_4$ is preferably methyl. $R_{11}$ may be a lower alkyl, alkenyl, hydroxyalkyl, or alkoxy group having up to about 3 carbon atoms; with the provision that the group has rotational flexibility around the first-bound carbon to allow the rest of the group to be positioned outside the plane of the texaphyrin. Thus, a preferred alkenyl is $CH_2CH=CH_2$. $R_{11}$ is most preferably a methyl group.

TABLE 2

REPRESENTATIVE SUBSTITUENTS FOR TEXAPHYRIN $2_G$ OF FIG. 2

| Cpd. | $R_1$ | $R_8$ | $R_7$ | $R_{11}$ |
|---|---|---|---|---|
| B1 | $OCH_2CH_2OH$ | $OCH_2CH_2CH_2OH$ | $OCH_2CH_2CH_2OH$ | $CH_3$ |
| B2 | $CH_2CH_3$ | $OCH_2CH_2CH_2OH$ | $OCH_2CH_2CH_2OH$ | $CH_3$ |
| B3 | $CH_2CH_2CH_2OH$ | $OCH_2CH_2CH_2OH$ | $OCH_2CH_2CH_2OH$ | $CH_3$ |
| B4 | $CH_2CH_2CH_2OH$ | $O(CH_2CH_2O)_3H$ | $O(CH_2CH_2O)_3H$ | $CH_3$ |
| B5 | $CH_2CH_2CH_2OH$ | $O(CH_2CH_2O)_3CH_3$ | $O(CH_2CH_2O)_3CH_3$ | $CH_3$ |
| B6 | $CH_2CH_2CH_2OH$ | $OCH_3$ | $OCH_2COOH$ | $CH_3$ |
| B7 | $CH_2CH_2CH_2OH$ | $OCH_2COOH$ | $OCH_2COOH$ | $CH_3$ |
| B8 | $CH_2CH_2CH_2OH$ | $O(CH_2CH_2O)_3CH_3$ | $OCH_2COOH$ | $CH_3$ |
| B9 | $CH_2CH_2CONHCH—(CH_2OH)_2$ | $OCH_2CH_2OH$ | $OCH_2CH_2OH$ | $CH_3$ |
| B10 | $CH_2CH_2CON—(CH_2CH_2OH)2$ | $OCH_2CH_2OH$ | $OCH_2CH_2OH$ | $CH_3$ |
| B11 | $CH_2CH_2CH_2OH$ | $O(CH_2CH_2O)_3CH_3$ | $OCH_3$ | $CH_3$ |
| B12 | $CH_2CH_2CH_2OH$ | $OCH_2CH_2CH_2COOH$ | H | $CH_2CH_3$ |
| B13 | $CH_2CH_2CH_2OH$ | $OCH_2CH_2CH_2OH$ | $OCH_2CH_2CH_2OH$ | $CH_2CH_3$ |
| B14 | $CH_2CH_2CH_2OH$ | $O(CH_2CH_2O)_3CH_3$ | $O(CH_2CH_2O)_3CH_3$ | $CH_2CH_3$ |
| B15 | $CH_2CH_2CH_2OH$ | $O(CH_2CH_2O)_3CH_3$ | $O(CH_2CH_2O)_3CH_3$ | $CH_2CH=CH_2$ |
| B16 | $CH_2CH_2CH_2OH$ | $O(CH_2CH_2O)_3CH_3$ | $O(CH_2CH_2O)_3CH_3$ | $CH_2CH_2OH$ |
| B17 | $CH_2CH_2CH_2OH$ | $O(CH_2CH_2O)_3CH_3$ | $O(CH_2CH_2O)_3CH_3$ | $CH_2CH_2OCH_3$ |
| B18 | $CH_2CH_2CH_2OH$ | $O(CH_2)_nCOOH$ where n = 1–7 | H | $CH_3$ |
| B19 | $CH_2CH_2CH_2OH$ | $O(CH_2CH_2O)_nCH_3$ where n = 1–200 | $O(CH_2CH_2O)_nCH_3$ where n = 1–200 | $CH_3$ |
| B20 | $CH_2CH_2CH_2OH$ | $OCH_2CON$-linker-oligonucleotide | H | $CH_3$ |
| B21 | $CH_2CH_2CH_2OH$ | $OCH_2CON$-linker oligonucleotide | $O(CH_2CH_2O)_3CH_3$ | $CH_3$ |
| B22 | $CH_2CH_2CH_2OH$ | $OCH_2CON$-linker site directing molecule | H | $CH_3$ |
| B23 | $CH_2CH_2CH_2OH$ | $O(CH_2)_nCOOH$ where n = 1–7 | H | $CH_2CH_2OH$ |
| B24 | $CH_2CH_2CH_2OH$ | $OCH_2CON$-linker oligonucleotide | H | $CH_2CH_2OH$ |
| B25 | $CH_2CH_2CH_2OH$ | $OCH_2CON$-linker oligonucleotide | $O(CH_2CH_2O)_3CH_3$ | $CH_2CH_2OCH_3$ |

TABLE 2-continued

REPRESENTATIVE SUBSTITUENTS FOR TEXAPHYRIN $2_G$ OF FIG. 2

| Cpd. | $R_1$ | $R_8$ | $R_7$ | $R_{11}$ |
|---|---|---|---|---|
| B26 | $CH_2CH_2CH_2OH$ | $OCH_2CH_2CH_2CON$-linker-site directing molecule | H | $CH_2CH_2OH$ |
| B27 | $CH_2CH_2CH_2OH$ | $O(CH_2)_nCON$-linker-site directing molecule where n = 1–7 | H | $CH_3$ |
| B28 | $CH_2CH_2CH_2OH$ | $O(CH_2)_nCON$-linker oligonucleotide where n = 1–7 | H | $CH_3$ |

EXAMPLE 3

Texaphyrin Site-Directing Conjugates

The use of texaphyrins as radiation sensitizers in vivo as part of a treatment procedure relies on the effective localization of the texaphyrin to the treatment site. Texaphyrins have intrinsic biolocalization properties, localizing in lipophilic tissue such a liver, tumor and atheroma, for example, as described in U.S. Pat. No. 5,252,720, incorporated by reference herein. Further localization specificity may be achieved by conjugating the texaphyrin or texaphyrin-metal complex to a site-directing molecule such as a polynucleotide or oligonucleotide, for example, an antisense oligonucleotide, as described in Example 4; a polyamide including a peptide having affinity for a biological receptor or a protein such as an antibody, low density lipoprotein (LDL) or the APO-protein of LDL; a steroid or steroid derivative; a hormone such as estradiol or histamine; a hormone-mimic such as morphine; a dye or other compound having binding specificity for a target; or a further macrocycle such as a sapphyrin or rubyrin.

Texaphyrins are especially suited for acting as bifunctional chelating agents in antibody conjugate-based treatment since they have functional groups suitable for conjugation to the antibody. They form covalent linkages that are stable in vivo and do not destroy the immunological competence of the antibody, they are relatively nontoxic, they bind metals and retain the metal of interest under physiological conditions, and they are readily soluble in a physiological environment. A further advantage of these texaphyrins is that many would be suitable for further functionalization. Treatment of carboxylated texaphyrins with thionyl chloride or p-nitrophenol acetate would generate activated acyl species suitable for attachment to monoclonal antibodies or other site-directing molecules of interest. Standard in situ coupling methods (e.g. 1,1'-carbonyldiimidazole (CDI)) cculd be used to effect the conjugation.

Another means of gaining selectivity may be to link covalently the texaphyrin complex to a sapphyrin molecule, (Sessler et al., 1992; Furuta et al., 1991; Sessler et al., 1991; U.S. Pat. No. 5,159,065; U.S. Pat. No. 5,120,411; U.S. Pat. No. 5,041,078). Since sapphyrins bind DNA, $K\sim 10^6 M^{-1}$, (U.S. Ser. No. 07/964,607, incorporated by reference herein) the linked texaphyrin-sapphyrin complex could effectively increase the texaphyria concentration at locations adjacent to the sapphyrin binding sites. Sapphyrins have a higher fluorescent quantum yield than texaphyrins, allowing greater fluorescence detection. A laser system may be employed where the molecules are optimized to the laser wavelength; an excited sapphyrin may transfer its energy to the conjugated texaphyrin for detection. The texaphyrin molecule may further be designed to pass through cell membranes for selective radiosensitization.

EXAMPLE 4

Texaphyrin-Oligonucleotide Conjugates

The present example provides synthetic procedures where a texaphyrin is coupled to an oligonucleotide or analog thereof, or is incorporated into the synthesis scheme of an oligonucleotide or analog thereof, to provide a texaphyrin-oligonucleotide or texaphyrin-oligonucleotide analog conjugate having binding specificity for a complementary oligonucleotide.

Amides, ethers, and thioethers are representative of linkages which may be used for coupling site-directing molecules such as oligonucleotide to texaphyrins. Oligonucleotides or other site-directing molecules functionalized with amines at the 5'-end, the 3'-end, or internally at sugar or base residues are modified post-synthetically with an activated carboxylic ester derivative of the texaphyrin. In the presence of a Lewis acid such as $FeBr_3$, a bromide derivatized texaphyrin will react with an hydroxyl group of an oligonucleotide to form an ether linkage between the texaphyrin linker and the oligonucleotide. Alternatively, oligonucleotide analogues containing one or more thiophosphate or thiol groups are selectively alkylated at the sulfur atom(s) with an alkyl halide derivative of the texaphyrin. Oligodeoxynucleotide-complex conjugates are designed so as to provide optimal catalytic interaction between the targeted DNA phosphodiester backbone and the texaphyrin.

For general reviews of synthesis of DNA, RNA, and their analogues, see *Oligonucleotides and Analogues*, F. Eckstein, Ed., 1991, IRL Press, New York; *Oligonucleotide Synthesis*, M. J. Gait, Ed., 1984, IRL Press Oxford, England; Caracciolo et al. (1989); *Bioconjugate Chemistry*, Goodchild, J. (1990); or for phosphonate synthesis, Matteucci, M D. et al., *Nucleic Acids Res.* 14:5399 (1986) (the references are incorporated by reference herein).

In general, there are three commonly used solid phase-based approaches to the synthesis of oligonucleotides containing conventional 5'-3' linkages. These are the phosphoramidite method, the phosphonate method, and the triester method.

A brief description of a current method used commercially to synthesize oligom(eric DNA is as follows: Oligomers up to ca. 100 residues in length are prepared on a commercial synthesizer, eg., Applied Biosystems Inc. (ABI) model 392, that uses phosphoramidite chemistry. DNA is synthesized from the 3' to the 5' direction through the sequential addition of highly reactive phosphorous(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add a further residue until the desired DNA polymer is synthesized. The full length polymer is released from the solid support, with concomitant removal of remaining protective groups, by exposure to base. A common protocol uses saturated ethanolic ammonia.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete. The phosphonates can also be converted to phosphoramidate derivatives by reaction with a primary or secondary amine in the presence of carbon tetrachloride.

In the triester synthesis, a protected phosphodiester nucleotide is condensed with the free hydroxyl of a growing nucleotide chain derivatized to a solid support in the presence of coupling agent. The is reaction yields a protected phosphate linkage which may be treated with an oximate solution to form unprotected oligonucleotide.

To indicate the three approaches generically, the incoming nucleotide is regarded as having an "activated" phosphite/phosphate group. In addition to employing commonly used solid phase synthesis techniques, oligonucleotides may also be synthesized using solution phase methods such as diester synthesis. The methods are workable, but in general, less efficient for oligonucleotides of any substantial length.

Preferred oligonucleotides resistant to in vivo hydrolysis may contain a phosphorothioate substitution at each base (*J. Org. Chem.*, 55:4693–4699, (1990) and Agrawal, (1990)). Oligodeoxynucleotides or their phosphorothioate analogues may be synthesized using an Applied Biosystem 380B DNA synthesizer (Applied Biosystems, Inc., Foster City, Calif.).

A further synthetic procedure inserts a texaphyrin directly into a nucleic acid synthesis scheme, preferably on a solid support. Texaphyrin macrocycles were not known to be stable under the basic conditions employed in the synthesis of oligonucleotides. For example, until the results presented herein were obtained, it was thought that texaphyrin, being a Schiff base, may be unstable to the basic conditions employed during oligonucleotide synthesis, specifically during the ammonia and ethanol cleavage and deprotection steps.

It is contemplated that the stepwise synthesis provided herein may be performed manually or may be automated, and may be in a solution-phase or on a solid support. Solid support synthesis may be accomplished using an automated or a manual nucleic acid synthesizer. Common solid supports are CPG (control pore glass) and CPS (control pore silica). Other possible solid supports include polystyrene, polyamide/Kieselguhr, and cellulose paper. A preferred embodiment of this method is automated synthesis on a solid support. Attachment of a texaphyrin to an oligonucleotide during stepwise synthesis obviates the need for a postmodification protocol and a second purification of the product. This results in an improved yield and greatly facilitates scale-up. The texaphyrin may be a free base texaphyrin or may be a texaphyrin metal complex.

The finding that Ln(III) texaphyrins, notably $DyT2B2^{2+}$ and $EuT2B1^{2+}$, are stable to treatment with ethanolic ammonia for 24 h at ambient temperature suggests that it is possible to derivatize oligomers with lanthanide(III) texaphyrin complexes during stepwise synthesis.

A texaphyrin or metal complex thereof may be inserted into the synthesis scheme of an oligonucleotide in a variety of ways. Possible linkages include amide, phosphate, thioether, amino, and ether linkages. An amide linkage represents the reaction of an activated carboxylic acid derivative of a macrocycle and an amino linker attached to an oligonucleotide. Activation may be achieved in solution phase or on a solid support using DCC and NHS, EDC (1-Ethyl-3-(3-dimethylaminopropyl) carbodiimide), or activated esters of NHS, nitrophenyl, pentachlorophenyl, acid anhydride, or sulfonyl chloride. In addition, for the solid support reaction, activation may be in the form of an acid chloride. A phosphate linkage represents the reaction of an activated phosphate derivative of a macrocycle and the 5' hydroxyl group on an oligonucleotide. The activated phosphate may be a phosphoramidite, an H-phosphonate, a triester, or a diester.

Figure 3A:
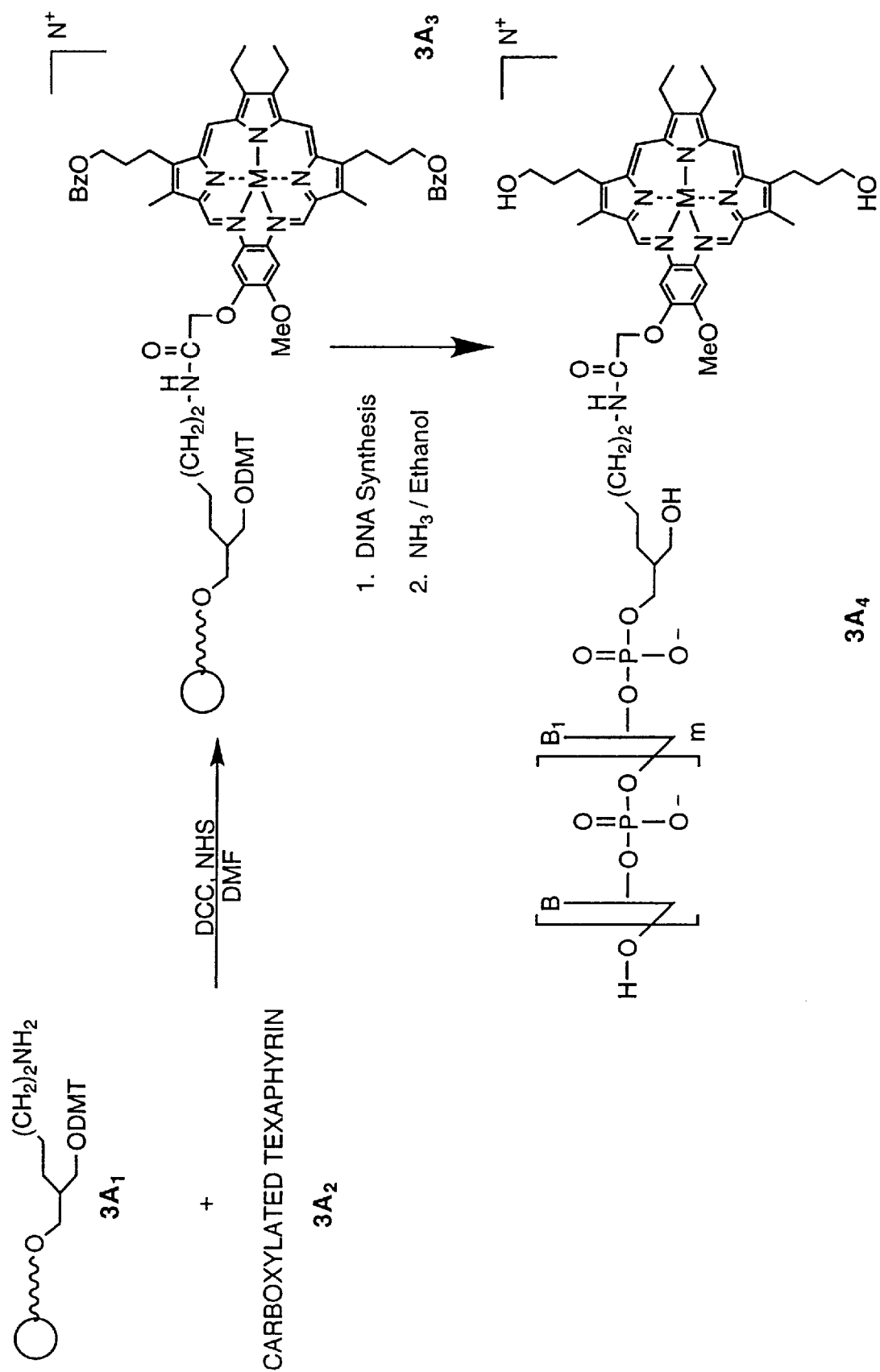
FIG. 3A, FIG. 3B, and FIG. 3C show stepwise synthesis schemes for preparing texaphyrin-metal complex-oligonucleotide conjugates.

Representative synthetic schemes are discussed here. In the approach depicted in FIG. 3A, a metal-texaphyrin complex $3A_2$ is attached to a solid support $3A_1$ via a six carbon amine linker. This amide-forming coupling reaction is currently employed to attach the complex post-synthetically. It is important to note that texaphyrin hydroxyl groups are protected as an ester on $3A_3$ for stepwise synthesis. These protecting groups are labile to the ethanolic ammonia treatment. Such a metal-texaphyrin-derivatized support may be used for stepwise synthesis, and upon cleavage and deprotection, results in a 3'-linked metal-texaphyrin-DNA conjugate $3A_4$. The amide-forming reaction may also occur at the conclusion of DNA synthesis before deprotection and cleavage from the solid support.

Figure 3B:
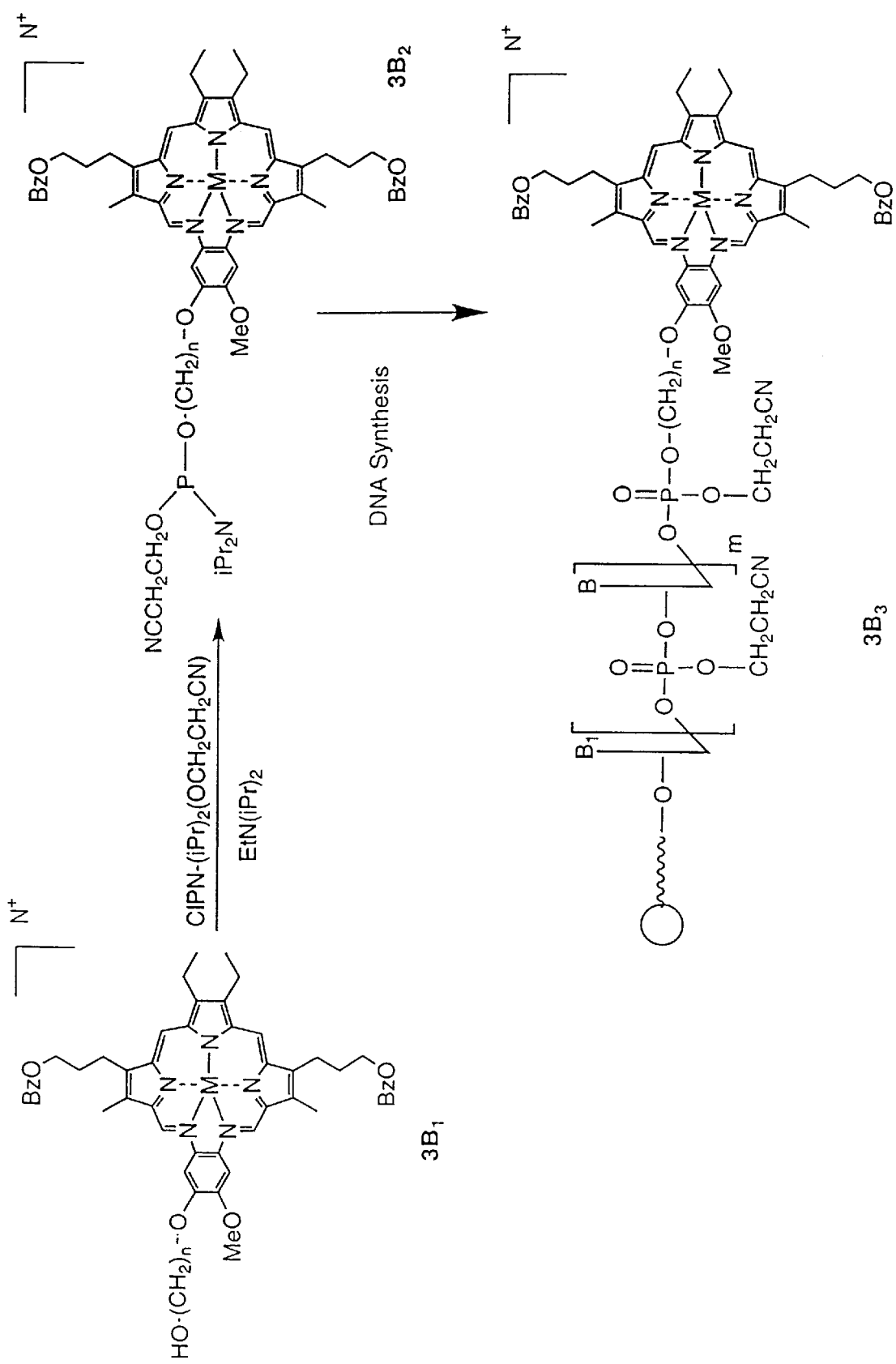
Figure 3C:
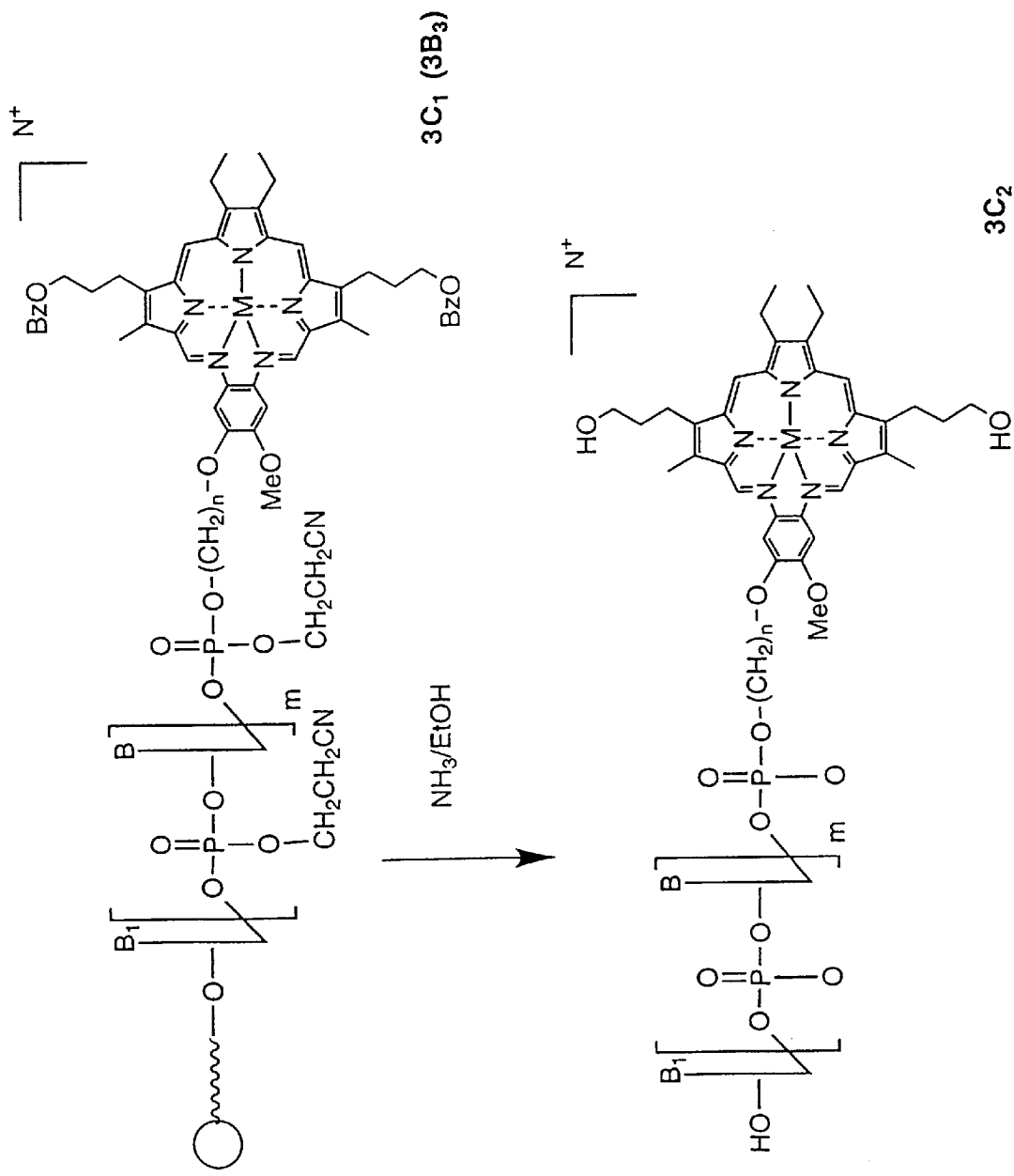

As depicted in FIG. 3B, a phosphoramidite derivative of a metal texaphyrin complex $3B_2$ is prepared by reaction of the monoalcohol $3B_1$ with phosphitylating agent and diisopropylethylamine. The hydroxyl groups are again protected as the ester for this synthesis. The resulting phosphoramidite is coupled on the synthesizer as the final residue to form $3B_3$. In this approach, deprotection results in a 5'-linked texaphyrin-metal complex-DNA conjugate $3C_2$. This texaphyrin-conjugate has no amide bonds in the linker.

A texaphyrin-DNA conjugate having the texaphyrin in an internal linkage to the oligonucleotide may be synthesized using this stepwise approach. A dihydroxytexaphyrin is treated with dimethoxytritylchloride in the presence of dimethylaminopyridine and pyridine. The resulting monoprotected texaphyrin is treated with phosphitylating agent and diisopropylethylamine to produce a monoprotected phosphoramidite. This product is coupled to a growing oligonucleotide during synthesis in place of a nucleotide residue to insert a texaphyrin in an internal linkage. The monoconjugate may then be further coupled to nucleotides to produce a texaphyrin-DNA conjugate having the texaphyrin in an internal linkage to the oligonucleotide. Additionally, phosphonate or phosphodiester derivatives of texaphyrin may be utilized to form similar internal, 3', or 5' linkages by the phosphonate or triester methods, respectively.

Oligonucleotide analog conjugates may be coupled to texaphyrins in a similar manner as herein described. In particular, phosphorothioates, 2'-O-methylated ribonucleotides, or other nucleic acid analogs such as methyl phosphonate derivatives are preferred due to the enhanced stability the derivatization provides towards nucleases in vivo. A texaphyrin-oligonucleotide conjugate of a derivatized RNA such as a 2'-O-methyl RNA analog may provide stability against self-cleavage. RNA is hydrolyzed by texaphyrin complexed with Lu; however, the 2'-O-Me RNA lacks a 2'-OH and, therefore, is stable to hydrolysis. Therefore, an RNA analog oligomer may be more stable than a DNA oligomer for the texaphyrin-oligonucleotide conjugate. The synthesis of RNA analog-conjugates is the same as for texaphyrin-DNA conjugates discussed previously herein. An RNA-analog conjugate may be complementary to an antisense or a sense strand of DNA and forms a triple helix in the process of binding to a double helix.

A further method for the synthesis of texaphyrin-oligonucleotide conjugates is to incorporate nucleotides enzymatically. A variety of DNA imd RNA polymerases may be used, however, the Klenow fragment of DNA polymerase I from *E. coli* and terminal deoxynucleotidyl transferase are preferred. Goodchild, J. (1990) provides a general discussion of the enzymatic synthesis of oligonucleotides and is incorporated by reference herein.

EXAMPLE 5

Radiation Sensitization of a Murine Leukemia Cell Line

This example describes the use of GdT2B2$^{2+}$ as a radiation sensitizer to enhance the radiolysis of a mouse L1210 leukemia cell line. The presence of the metal is not important for the radiation sensitization properties of texaphyrins; however, the metal contributes stability to the texaphyrin complex. A metal texaphyrin complex with its counterions is considered a neutral complex for purposes of this application; for example, GdT2B2(OAc)$_2$ is a neutral complex. A metal complex of texaphyrin, such as GdT2B2$^{2+}$ has two positive charges. When GdT2B2$^{2+}$ picks up an electron, it becomes a short-lived $\pi$-radical cation, GdT2B2$^{+\bullet}$. The $\pi$-radical cation picks up a proton or rearranges to the texaphyrin radical, GdT2B2(H)$^{2+\bullet}$, which has significant stability as described below.

Physical Studies

The radiation chemistry of Gd-T2B2$^{2+}$ was studied by the technique of pulse radiolysis wherein a short burst of ionizing radiation (100 ns duration at 4 MeV) was injected into an aqueous solutior of Gd-T2B2$^{2+}$ and the subsequent reactions were monitored by absorption spectroscopy. The solution conditions were varied so as to optimize the radiation chemistry in favor of reaction with hydroxyl radicals or hydrated electrons. First, aqueous solution (pH 7) containing Gd-T2B2$^{2+}$ (1×10$^{-4}$ M) was saturated with nitrous oxide so as to convert the hydrated electrons into a second crop of hydroxyl radicals:

$$e_{aq}^{-}+N_2O+H_2O\rightarrow N_2+OH^{-}+OH^{\bullet}$$

According to absorption spectroscopy there was no obvious reaction between hydroxyl radicals and Gd-T2B2$^{2+}$ under these conditions. Second, the aqueous solution (pH 7) containing Gd-T2B2$^{2+}$ (1×10$^{-4}$ M) was saturated with nitrogen after addition of isopropanol (0.1 M). In this case, hydroxyl radicals formed in the primary radiolysis event abstract the tertiary hydrogen atom from isopropanol, forming the acetone ketyl radical:

$$OH^{\bullet}+(CH_3)_2CHOH\rightarrow H_2O+(CH_3)_2C^{\bullet}OH$$

This latter species is a powerful reducing agent and, consequently, these reaction conditions provide a reducing environment. Both the hydrated electron and the acetone ketyl radical reduce Gd-T2B2$^{2+}$ in a one-electron process. The one-electron reduction potential measured by cyclic voltametry for Gd-T2B2$^{2+}$ was found to be about 0.08 V vs. NHE and, therefore, the compound is readily reduced in aqueous solution.

$$Gd\text{-}tex^{2+}+e_{aq}^{-}\rightarrow Gd\text{-}tex^{+\bullet}$$

$$Gd\text{-}tex^{2+}+(CH_3)_2C^{\bullet}OH\rightarrow Gd\text{-}tex^{+\bullet}+(CH_3)_2CO+H^{+}$$

The resultant $\pi$-radical cation of Gd-T2B2$^{2+}$, Gd-T2B2$^{+\bullet}$, is readily detected from absorption spectral changes, and was found to decay over approximately 200 microseconds. This reaction does not result in restoration of Gd-T2B2$^{2+}$ and its rate increases with decreasing pH. On this basis, the observed reaction is attributed to protonation of the $\pi$-radical cation:

$$Gd\text{-}tex^{+\bullet}+H^{+}\rightarrow Gd\text{-}tex(H)^{2+\bullet}$$

The protonated radical, Gd-T2B2(H)$^{2+\bullet}$, decays very slowly, having a lifetime of about 30 seconds, by complex reactions that did not restore the original Gd-T2B2$^{2+}$. The lifetime of this radical is not affected by the presence of oxygen.

Additional pulse radiolysis experiments showed that Gd-T2B2$^{+\bullet}$ was formed by reduction of Gd-T2B2$^{2+}$ with superoxide ion (O$_2^{-}$), carbon dioxide $\pi$-radical anion (CO$_2^{-}$), and the carbon-centered radicals formed by hydrogen abstraction from ethanol and methanol. Furthermore, it was shown that the protonated radical was formed by reaction between hydrogen atoms and GdT2B2$^{2+}$.

$$Gd\text{-}tex^{2+}+H^{\bullet}\rightarrow Gd\text{-}tex(H)^{2+\bullet}$$

It is clear, therefore, that under radiolytic conditions all the reducing equivalents can be utilized to reduce Gd-T2B2$^{2+}$ to Gd-T2B2(H)$^{2+\bullet}$, regardless of the reaction conditions.

Experimental Conditions. For cytotoxicity studies, the radiation source was a Phillips 50 KVP constant potential X-ray generator, model 120.102.1 equipped with a Machlett OEG60 X-ray tube. Dosimetry was made with the Friecke dosimeter. This system delivers 110 rads per minute into a target area of about 2 cm diameter. Samples were contained in petri dishes mounted into a 12 well tray. Three unirradiated dishes and 3 dishes containing cells without GdT2B2$^{2+}$ served as control experiments. Six dishes containing cells and GdT2B2$^{2+}$ were exposed to radiation for a predetermined period. A mechanical arm moved the tray after each exposure. After radiolysis, cells were incubated for 24 hours and cell viability was established by both methyl red concentration and trypan blue exclusion methods using conventional cell counting techniques. All experiments were conducted with log phase cells (5×10$^5$ cells per mL). Mouse leukemia L1210 cells were maintained in RPMI 1640 cell culture medium.

A stock solution of GdT2B2$^{2+}$ (1 mM) was prepared in purified water and small aliquots were added to cell suspensions (5×10$^5$ cell per mL) The mixture was incubated for 1 hour at 37° C. before being isolated, washed, and resuspended in nutrient solution. In most cases, the concentration of GdT2B2$^{2+}$ was 80 $\mu$M as measured by absorption spectroscopy.

Radiation-induced cleavage of intracellular DNA (or RNA) was measured by alkaline elution chromatography. Polyvinylchloride filters (pore size 2 μm) were used. Samples were exposed to a total of 20 Gy radiation.

Figure 4:
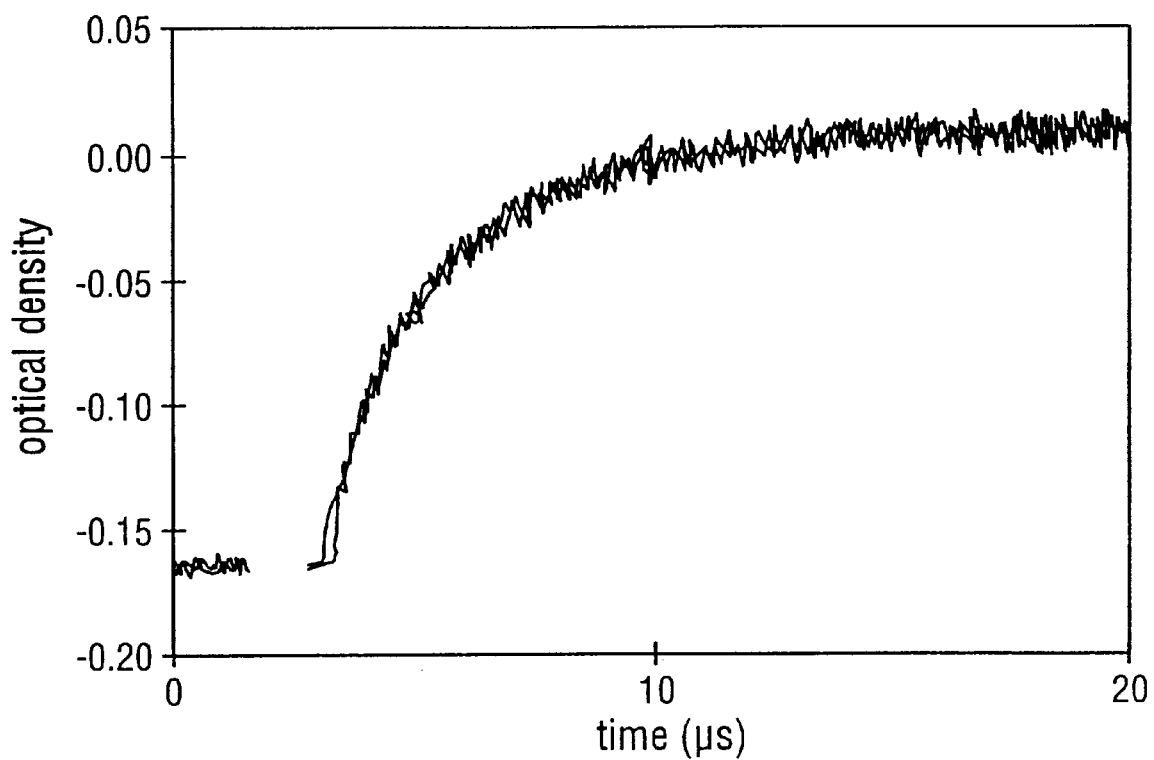
FIG. 4 shows pulse radiolysis; in aqueous isopropyl alcohol. The optical density is plotted versus time in μseconds for the formation of the gadolinium texaphyrin π-radical cation, GdT2B2$^{+\cdot}$.
Figure 5A:
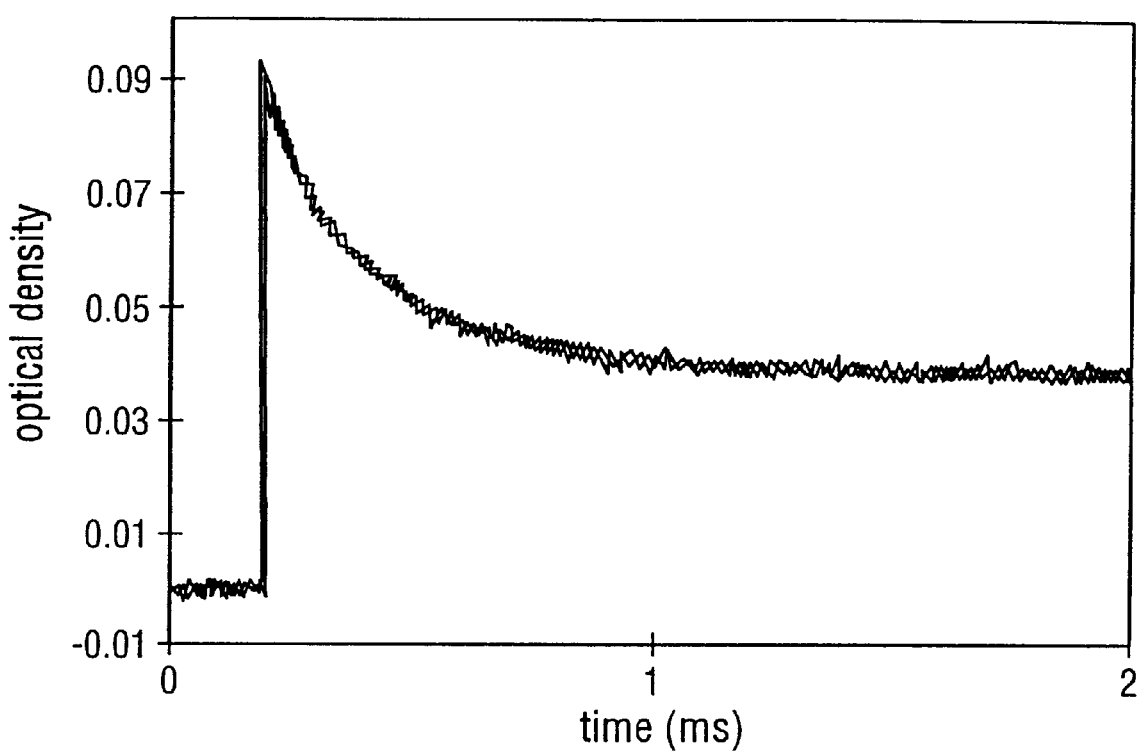
FIG. 5A and FIG. 5B show the decay of the π-radical cation formed in FIG. 4 versus time in mseconds. The plot in 5A demonstrates that the cation has a long half life [k=(1.7±0.5)×10$^9$ M$^{-1}$ s$^{-1}$] that is not affected by the presence of oxygen as shown in 5B [k=(1.9±0.7)×10$^9$ M$^{-1}$ s$^{-1}$]. These data indicate that the GdT2B2$^{+\cdot}$ π-radical cation has a lower reduction potential than oxygen and therefore does not pass its electrons to oxygen.
Figure 5B:
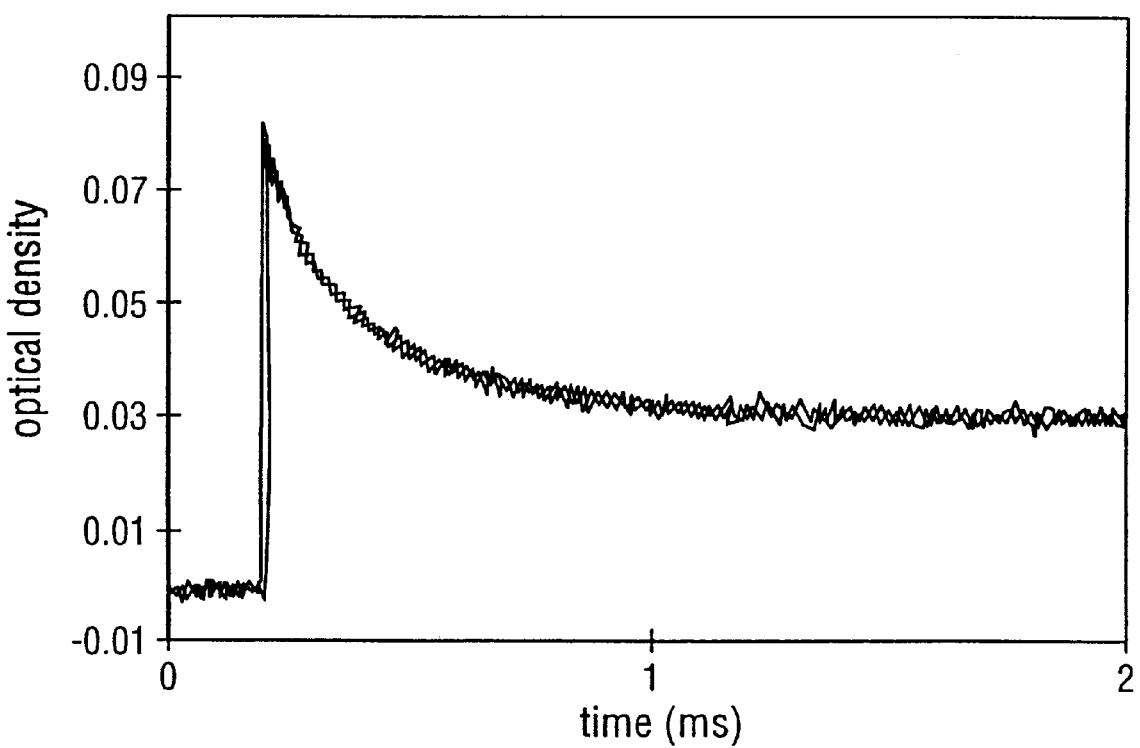

Results. Pulse radiolysis experiments carried out with GdT2B2$^{2+}$ in aqueous isopropanol are demonstrated in FIGS. 4, 5A and 5B. FIG. 4 demonstrates GdT2B2$^{+\cdot}$ π-radical cation formation. FIG. 5A demonstrates the π-radical cation decay in an oxygen free solution and in 5B, decay in the presence of O$_2$. The data indicate the remarkable stability of the GdT2B2$^{+\cdot}$ π-radical cation and demonstrate that GdT2B2$^{+\cdot}$ does not pass its electrons to oxygen, nor is it affected by the presence of oxygen. The data suggest the following intermediate radiolysis products for GdT2B2$^{2+}$:

TABLE 3

Pulse Radiolysis in Aqueous Isopropanol

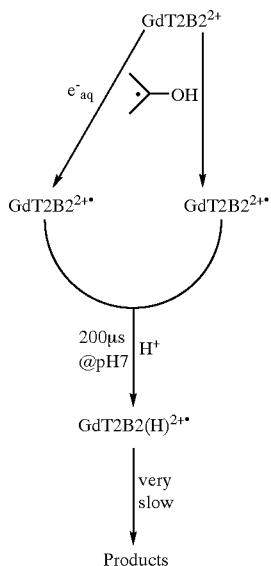

The GdT2B2$^{+\cdot}$ π-radical cation has a half life of less than 2 milliseconds. It picks up a proton or rearranges to the texaphyrin radical, GdT2B2(H)$^{2+\cdot}$, which has significant stability and a relatively long half life of about 30 seconds.

Figure 6:
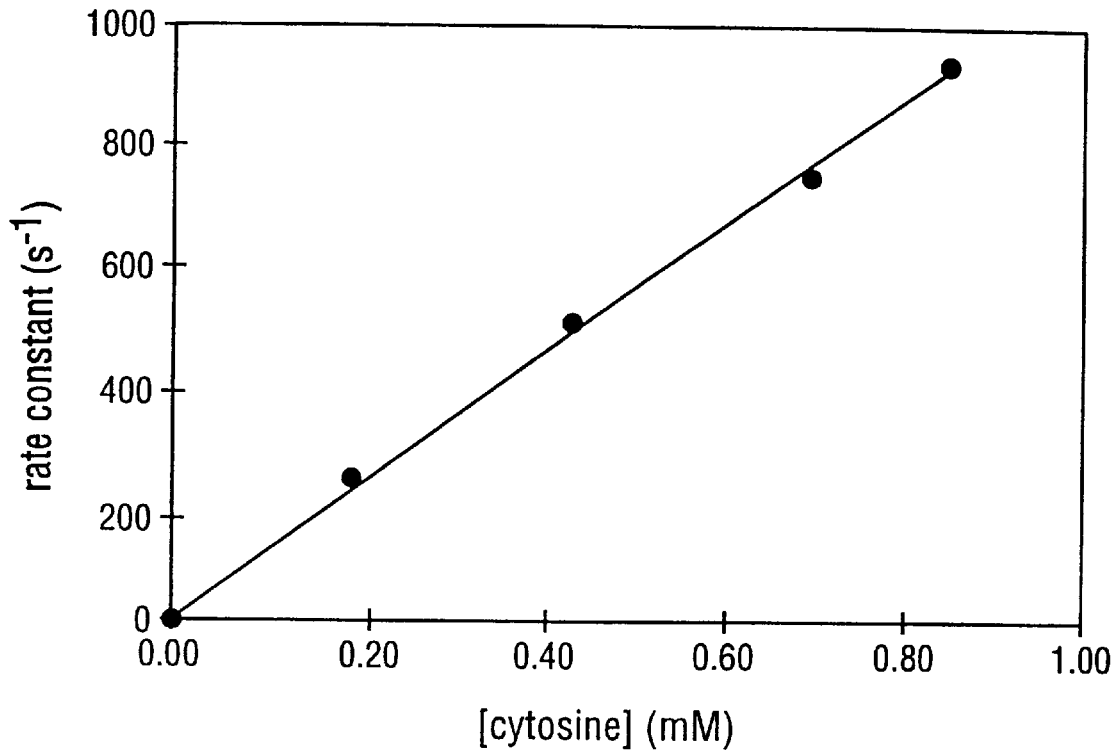
FIG. 6 shows the rate constant for the covalent modification of cytosine by the texaphyrin radical, GdT2B2(H$^\cdot$), (k$_2$≈10$^6$ M$^{-1}$ s$^{-1}$). These data indicate that the texaphyrin radical, while relatively stable, is nevertheless reactive and will cause damage to neighboring molecules.

Data in FIG. 6 present the rate constant for the reaction of the GdT2B2(H)$^{2+\cdot}$ radical with cytosine, one of the four nucleotide bases of DNA and RNA. It appears that GdT2B2(H)$^{2+\cdot}$ formed a covalent bond with cytosine, this reaction would probably inactivate the nucleic acid to which it bound.

Texaphyrin, therefore, has three advantageous properties for use as a radiation sensitizer:

i) The low redox potential of texaphyrin causes hydrated electrons to flow to texaphyrin allowing OH$^-$ to cause damage.
  ii) The texaphyrin radical is relatively stable, yet reacts readily to modify neighboring molecules covalently.
  iii) Texaphyrin may be particularly effective for treating the hypoxic areas of solid neoplasms because of intrinsic biolocalization and its indifference to the presence or absence of O$_2$. It may "replace" oxygen as a redox cycle.

Figure 7:
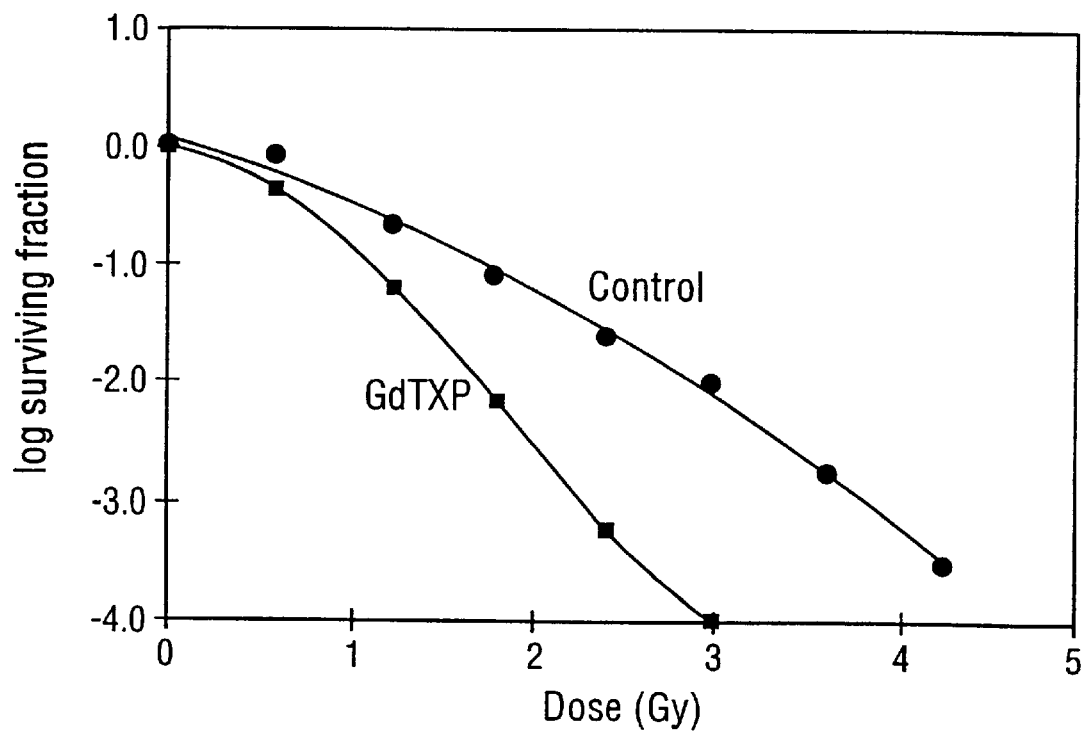
FIG. 7 shows the killing of mouse L1210 cells versus dose of radiation (in Grays) in the presence and absence of 20 μM GdB2T2$^{2+}$. The sensitizer enhancement ratio is 1.62.

FIG. 7 presents data from an experiment in which mouse L1210 cells were exposed to 20 μM GdT2B2$^{2+}$ and radiation. The control curve represents cell kill in the absence of GdT2B2$^{2+}$, the curve labeled GdTXP represents cell kill in the presence of GdT232$^{2+}$. A sensitizer enhancement ratio (SER) is the ratio of the dose needed to kill 95% of the cells without GdT2B2$^{2+}$ divided by the dose needed to kill 95% of the cells with GdT2B2$^{2+}$. If the sensitizer had no effect, the ratio would be 1.0; a very effective sensitizer would have a ratio of 3.0. The data of FIG. 7 indicate that at 20 μM, GdT2B2$^{2+}$ has an SER of 1.62. (An SER above 1.5 is clinically significant). Two further methods for measuring SER are the following: i) The slopes are compared where the curve is linear; SER is the ratio of the slope of the compound to the slope of the control, or ii) At a particular dose that is useful or clinically important, the ratio of number (or %) of cells killed in the control is compared to the number (or %) of cells killed by the compound.

Figure 8:
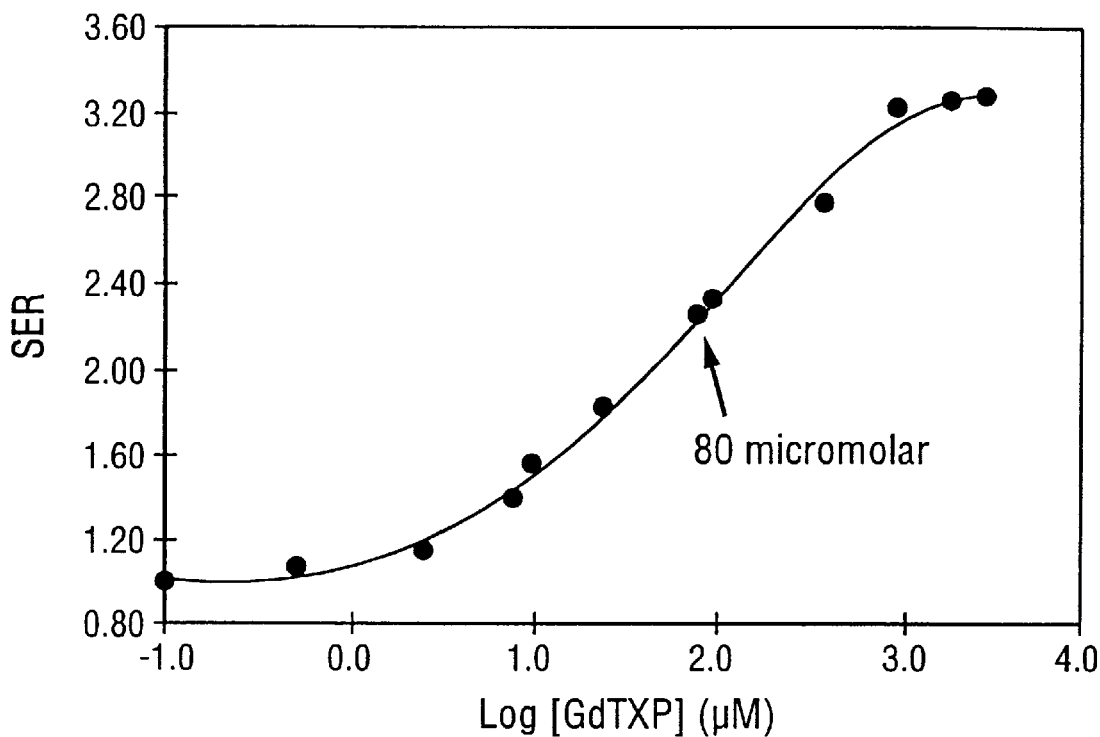
FIG. 8 shows the effect of GdB2T2$^{2+}$ on L1210 cell kill. Sensitizer enhancement ratios are plotted versus concentration of GdB2T2$^{2+}$. An SER greater than 1.5 is clinically significant. These data indicate that the effectiveness of GdB2T2$^{2+}$ as a sensitizer increases with the concentration achieved.

The SER increases with increasing concentrations of GdT2B2$^{2+}$ as indicated in FIG. 8. For example, at 80 μM, the SER is greater than 2.2, indicating that the highest physiologically tolerable level of GdT2B2$^{2+}$ is desirable for radiosensitization purposes.

Figure 9:
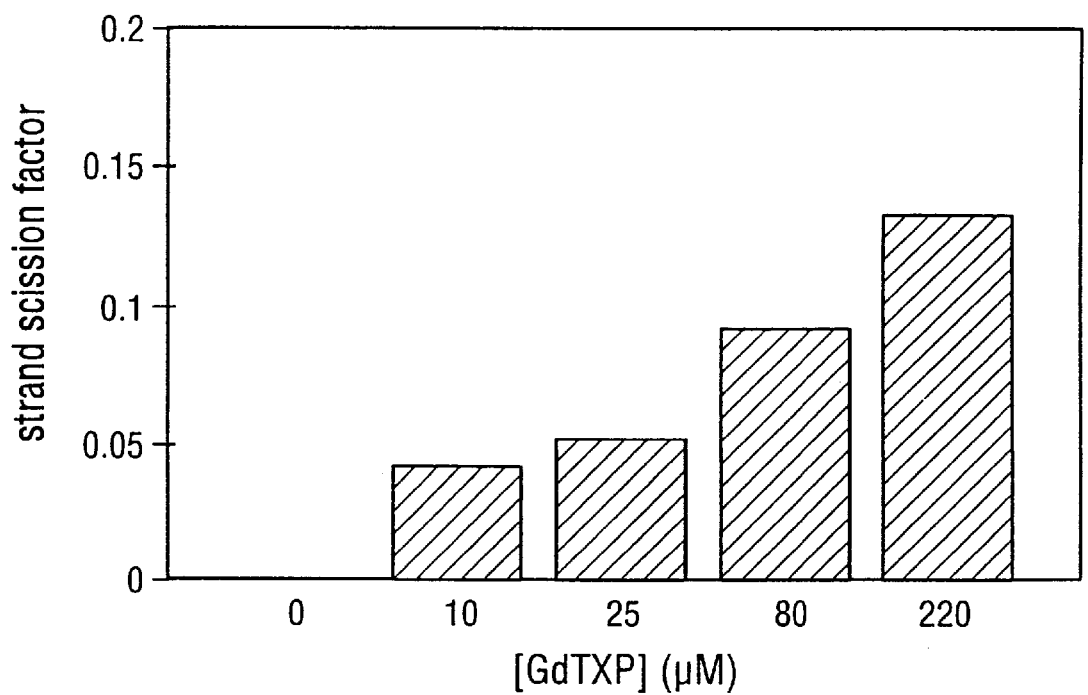
FIG. 9 shows the effect of Gd32T2$^{2+}$ on nucleic acid strand scission under radiolysis at 25 grays. L1210 cells were exposed to GdB2T2$^{2+}$ at the indicated concentrations, lysed and the nucleic acid material passed through a size selection filter.

Total nucleic acid samples obtained from L1210 cells exposed to a total of 20 Gray radiation and varying levels of GdT2B2$^{2+}$ were passed through a size selection filter (one Gray is a unit of absorbed radiation dose equal to 100 rads). The data of FIG. 9 indicate that no nucleic acid passed through the filter in the absence of GdT2B2$^{2+}$ and that, in the presence of GdT2B2$^{2+}$, nucleic acid was cleaved into fragments that passed through the filter. A larger amount of fragments was produced with higher levels of GdT2B2$^{2+}$ exposure. Clearly, nucleic acid strand scission occurs as a result of radiation in the presence of GdT2B2$^{2+}$. It is probable that the hydroxyl radical is responsible for the strand scission.

The radiosensitization properties of the texaphyrins described herein may allow reduced doses of radiation to be effective in treatment of an individual. Therefore, radiation side effects such as nausea and damage to normal cells may be lessened when treatment includes the use of texaphyrins of the present invention. Expected dose levels for an individual may range from 2–20 μmol/kg administered in multiple doses (e.g. before each fraction of radiation).

This radiation sensitization property of texaphyrins is independent of the inserted metal and is a function of the texaphyrin ligand only (i.e. Gd(III) ion is not reduced in this process). In vitro and in vivo studies on the gadolinium texaphyrin complexes also suggest their potential to enhance radiation damage, and since this enhancement is unaffected by the presence of oxygen, texaphyrins have the potential to increase damage in both oxic and hypoxic tumor cells.

EXAMPLE 6

Radiation Sensitization of a Huran Carcinoma Cell Line

This example describes the use of three texaphyrins according to the present invention as radiation sensitizers to enhance the radiolysis of a human HT-29 colonic adenocarcinoma cell line in vitro.

HT-29 cells maintained in RMPI 1680 nutrient medium were incubated with various concentrations of either GdT2B2$^{2+}$, GdT2BET$^{2+}$ or LuT2BET$^{2+}$ texaphyrin for 24 hr at 37° C. After incubation, the cells were harvested, washed, and resuspended in nutrient medium. Aliquots of cell suspensions (5 mL; 5×10$^5$ cells per mL) were placed on sterilized petri dishes and exposed to radiolysis for varying times. The radiation dose was calibrated by Fricke dosimetry. After radiolysis, the cells were incubated at 37° C. for 7 days, after which cell viability was assessed by the trypan blue exclusion method. Results were expressed in terms of logarithm of the survival fraction relative to non-irradiated cells. The controls were carried out with cells not exposed to the texaphyrin but irradiated under identical conditions.

Figure 10A:
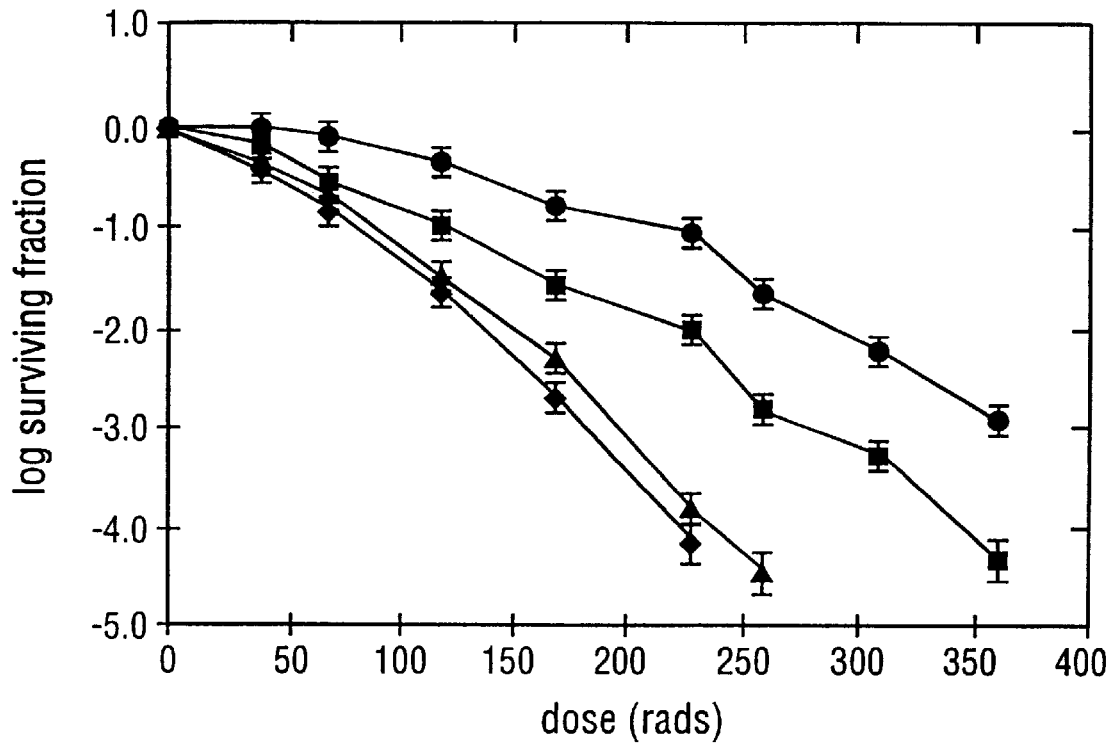
FIG. 10A and FIG. 10B show radiation sensitization of human HT-29 tumor cells using texaphyrins.

The results for the compounds at 20 µM concentration are presented in FIG. 10A, and show that, in the presence of each of the texaphyrins (GdT2B2$^{2+}$, ▲; GdT2BET$^{2+}$, ♦; and LuT2BET$^{2+}$, ■), enhanced cell kill resulted.

Figure 10B:
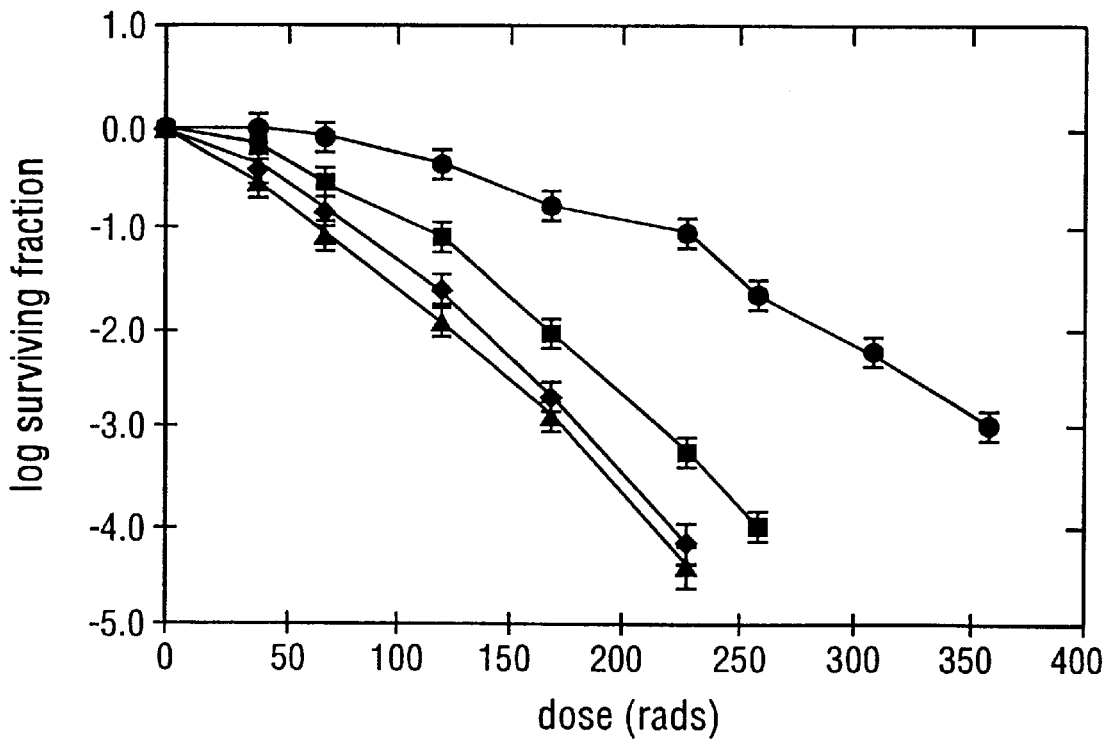

As was true for GdT2B2$^{2+}$, the sensitizer enhancement ratio (SER) increased with increasing concentrations of each of GdT2BET$^{2+}$ and LuT2BET$^{2+}$, as illustrated in Table 4 below and in FIG. 10B. FIG. 10B also shows cell kill in the absence (a) and presence of GdT2BET$^{2+}$ at three concentrations (b, 10 µM; c, 20 µM; d, 40 µM).

TABLE 4

Sensitization of HT-29 Cells

| Sensitizer | Concentration (µM) | SER |
|---|---|---|
| GdT2B2$^{2+}$ | 10 | 1.51 |
|  | 20 | 1.92 |
|  | 30 | 2.04 |
|  | 40 | 2.30 |
| GdT2BET$^{2+}$ | 10 | 1.59 |
|  | 20 | 2.08 |
|  | 30 | 2.21 |
|  | 40 | 2.45 |
| LuT2BET$^{2+}$ | 10 | 1.27 |
|  | 20 | 1.33 |
|  | 30 | 1.42 |
|  | 40 | 1.47 |

In vitro studies performed to determine the SERs for 20 µM GdT2B2$^{2+}$ using various human (HT29) and mouse (L1210, VA13, and RIF-1) cell lines indicate significant radiation sensitization (SERs of 1.92, 1.62, 1.52, and 1.05, respectively). Of special note is the SER of 1.92 since this suggests that GdT2B2$^{2+}$ provides significant radiation sensitization in a human cell line, the human colon carcinoma cell line HT29.

A comparison of the T2B2 gadolinium complex and the T2BET gadolinium complex provided comparable SER results in HT29 cells at all measured concentrations. The comparable radiation sensitization of HT29 cells at 20 µM for T2B2 (SER=1.92) and T2BET (SER=2.08) are shown in Table 4. Based on these results, the two compounds are considered comparable radiation sensitization agents. In addition, the radiation sensitization following exposure of HT29 cells to 10, 20, and 40 µM of T2BET (table 4) shows significant radiation sensitization with T2BET (SERs=1.59, 2.08, and 2.45, respectively).

These experiments indicate that gadolinium texaphyrin complexes are very easily reduced under pulse radiolysis conditions. This process is not dependent on oxygen. The reduced gadolinium texaphyrin radical is able to modify covalent cytosine bonds and perhaps intracellular DNA. In vitro studies using human and mouse cell lines indicate significant radiosensitization. This radiosensitization is not dependent on oxygen or on cell replication since incorporation into DNA is not involved in the mechanism of texaphyrin-induced radiosensitization.

EXAMPLE 7

Radiation Sensitization In Vivo

The present example provides data demonstrating the in vivo radiation sensitizer effect of texaphyrin T2BET.

A donor mouse bearing an SMT6 tumor was euthanized and the tumor was removed from the leg under aseptic conditions. The viable cell number was microscopically estimated and then 4–6 million cells were injected into a leg of a recipient tumor-free mouse while under anesthesia. Tumors in the recipient mice underwent a 4–7 day growth phase, dependent on the growth rate of the cells, before radiation treatment.

On the day of radiation treatment, mice with tumors of approximately equal size were selected. Gadolinium texaphyrin GdT2BET$^{2+}$ (2 µmol/mL) was administered intravenously by injection in the tail vein. Mice were treated with radiation 2 or 5 hours later. A 250 KV Phillips X-ray machine and a special mouse leg jig, with a lead shield, were used. The mouse was positioned prone inside a jig in such a way that only the right leg, with the tumor, was exposed to the X-ray. A single dose of 10, 20, 30, 40 or 50 Gray of radiation was administered. Six studies were run, averaging 4 test animals in each control and dosage group. Mortality and disease-free survival data were acquired as well as periodic measurements of tumor size for up to 75 days following radiation therapy. Kaplan-Meier survival curves were plotted and p-values were determined by log rank analyses of the curves.

Figure 11A:
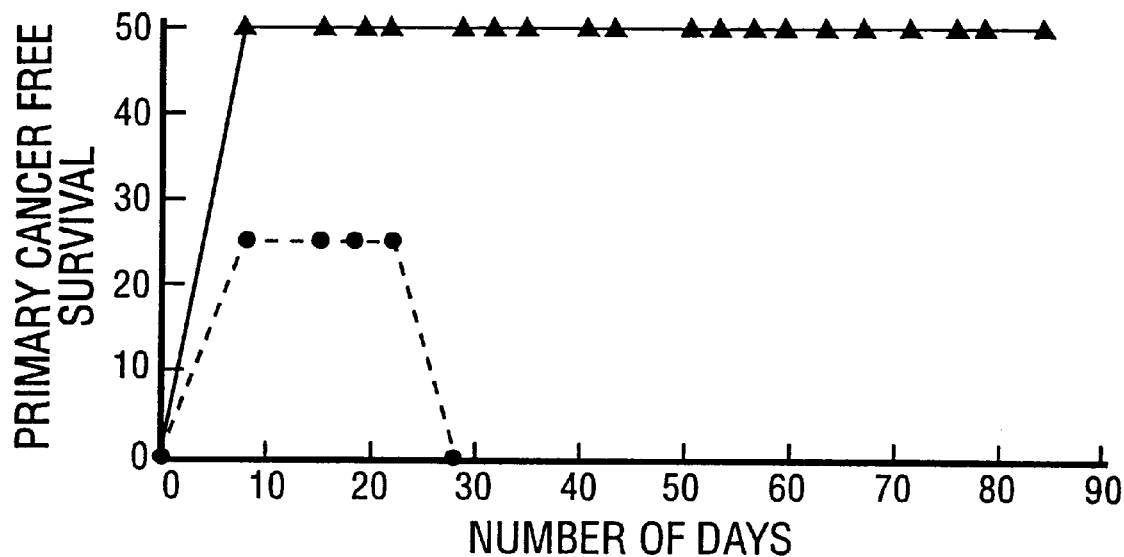
FIG. 11A, FIG. 11B, FIG. 11C and FIG. 11D show overall survival and primary cancer-free survival (complete responders) for animals administered radiation and T2BET (40 $\mu$mol/kg injection) ard those given radiation alone (control) for all animals dosed at 20 Gray (FIG. 11A and FIG. 11B) and 30 Gray (FIG. 11C and FIG. 11D). Four animals were in eaach group and radiation occurred 2 hours after the texaphyrin injection. Symbols are: ○, radiation only, overall survival; •, radiation only, cancer-free survival; Δ, T2BET and radiation, overall survival; ▲, T2BET and radiation, cancer-free survival.
Figure 11B:
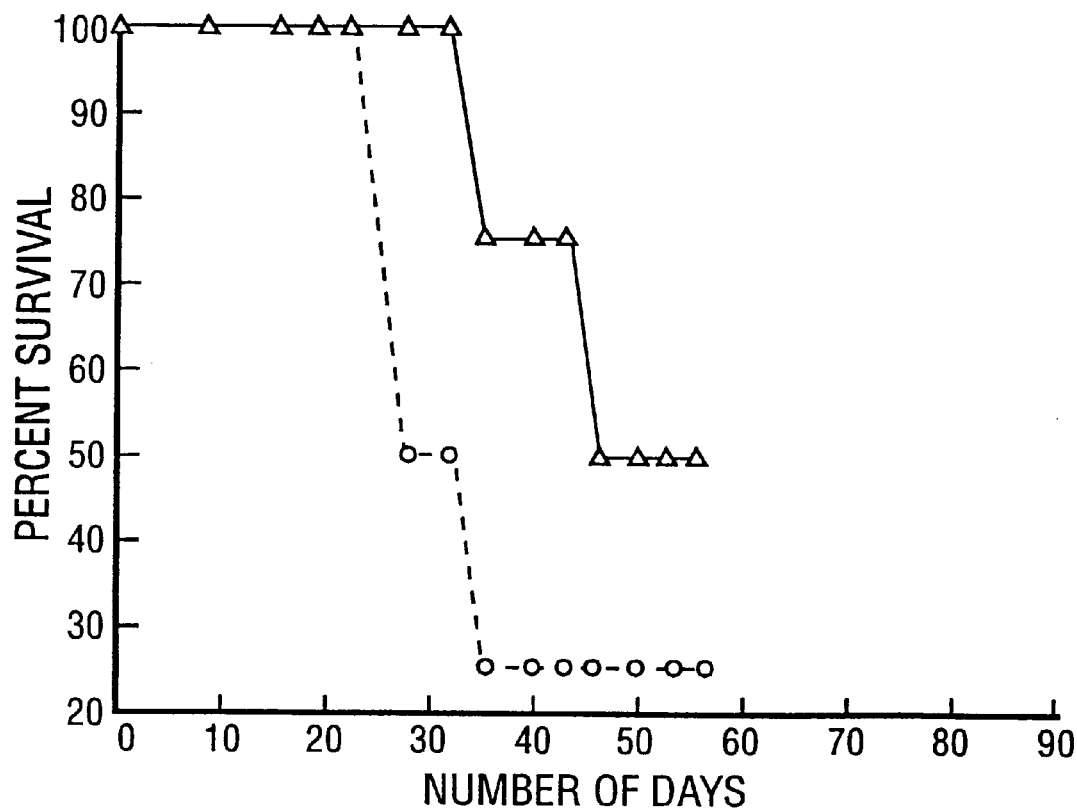
Figure 11C:
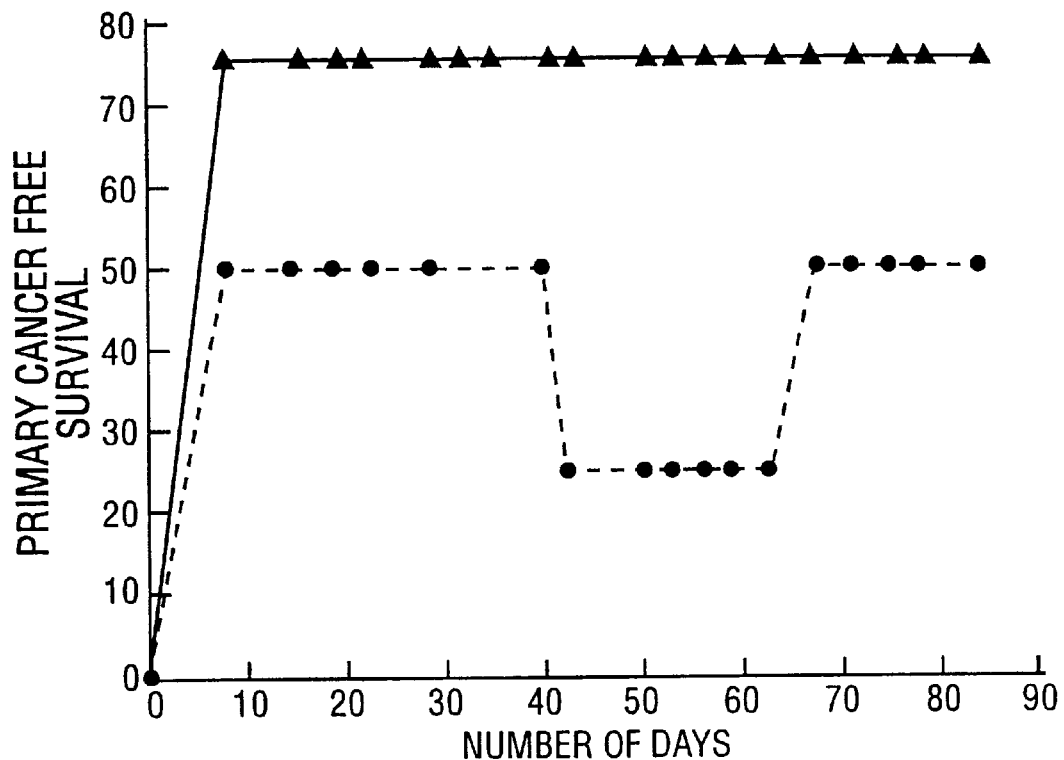
Figure 11D:
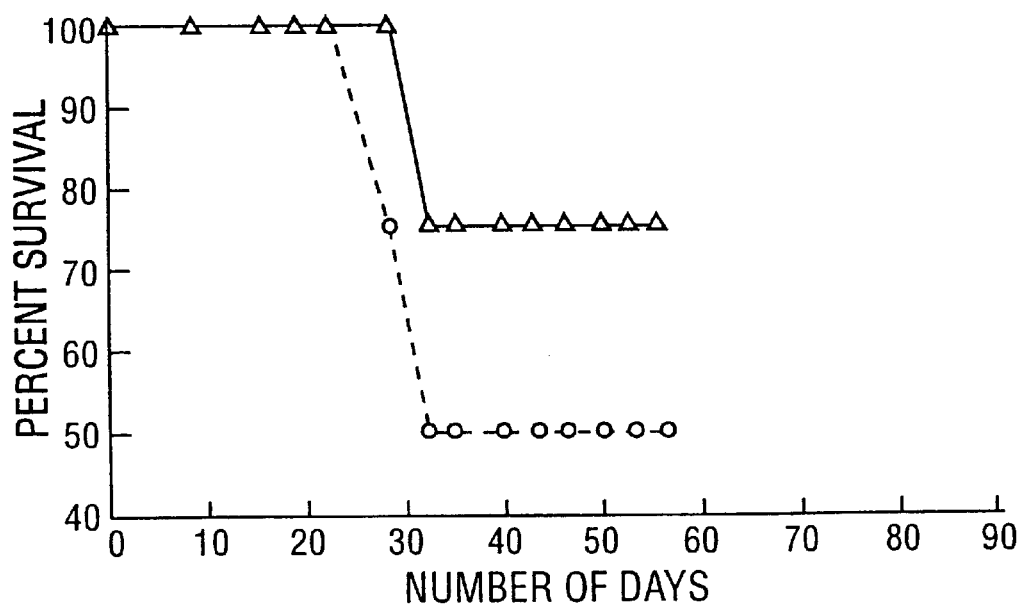

The experiments demonstrated that GdT2BET$^{2+}$ injection plus radiation improved the therapeutic results in all groups evaluated in comparison to the controls. In comparison to animals that received only radiation, is statistical significance was only achieved in animals receiving a radiation dose of 30 Gray. Log rank analyses of the Kaplan-Meier survival curves for 10 Gray (p=0.86) and 20 Gray (p=0.50) animals (FIGS. 11A–11B) are not much different with and without GdT2BET$^{2+}$, but the curves diverge for the 30 Gray (p=0.03) animals (FIGS. 11C–11D). The curves for 40 (p=0.60) and 50 Gray (p=0.97) do not demonstrate any statistically significant difference in treatment. The studies that did not show statistical significance, however, are based on fewer numbers of animals.

The data indicate that the 30 Gray dose of radiation produces partial control of tumor growth, which could be potentiated by T2BET injection (FIGS. 11C–11D). Lower doses of radiation are not adequate to observe a benefit from the administration of T2BET injection. At higher doses, tumor response is very good in both control (radiation alone) and T2BET injection plus radiation-treated animals, making it difficult to observe benefit of treatment with the sensitizer.

Efficacy of T2BET injection as a radiation sensitizer was also demonstrated in these studies by plotting survival and cancer-free (primary site) survival (FIGS. 11A–11D). Tumor growth delay was also greater in animals receiving both radiation (animals dosed at 30, 40, and 50 Gray) and the T2BET injected radiation sensitizer.

EXAMPLE 8

Radiation Sensitization Combined with Localization and/or Photodynamic Therapy

This example describes the use of texaphyrins in combined methods of localization and radiation sensitization, and radiation sensitization combined with PDT for destruction of neoplastic tissue and atheroma. A method of radiation sensitization is combination with localization by reference to a detectable texaphyrin is as follows. A detectable texaphyrin is administered to a host harboring a neoplasm or atheroma. Localization sites in the host are determined by reference to the texaphyrin. Localization means may be fluorescent spectroscopy, especially when the texaphyrin is nonmetallated or is complexed with a diamagnetic metal; magnetic resonance imaging when the texaphyrin contains a metal that is paramagnetic; gamma camera body scanning when the metal is gamma emitting; or by using diagnostic x-rays, especially mono- or polychromatic x-rays with energy around the K electrons of metals bound to texaphyrin. Gamma emitting metals for radioimmunodiagnostics are described in U.S. Pat. No. 5,252,720, incorporated by reference herein. A preferred gamma emitting metal is $^{111}$In (III). Texaphyrin-paramagnetic metal complexes would afford the advantage of visualization of the tumor by MRI. Preferred paramagnetic metals are Gd(III), Fe(III), or Mn(II), and a most preferred paramagnetic metal is gadolinium. The opportunity to combine imaging with radiotherapy is appealing since definition of treatment fields is an important component of radiotherapy delivery. In vivo experiments with GdT2BET$^{2+}$ injection in mice and rabbits have demonstrated that GdT2BET$^{2+}$ injection produces good contrast enhancement of tumors with doses as low as 5 μmol/kg and biodistribution studies with $^{14}$C-labeled GdT2BET$^{2+}$ have shown good differentiation between tumor and surrounding tissue.

Although GdT2BET$^{2+}$ has light-absorbing capabilities in the visible portion of its electronic spectra (major absorption peaks at about 415, 473, and 739 nanometers), it is not a photosensitizer because the Gd unpaired electrons immediately quench the excited state of the organic ligand induced by light. Free base texaphyrins or texaphyrins complexed with diamagnetic metals are photosensitive and generate singlet oxygen upon photoirradiation.

A method of radiation sensitization in combination with photodynamic therapy is as follows. A texaphyrin is administered to a host harboring benign or malignant neoplasm cells or atheroma. The texaphyrin exhibits radiosensitization properties and selective biolocalization in benign or malignant neoplasm cells or atheromatous plaque relative to surrounding tissue. Localization sites in the host are determined by reference to the texaphyrin using, for example, magnetic resonance imaging when a paramagnetic metal complex of texaphyrin is administered, fluorescence when a free-base texaphyrin or a texaphyrin diamagnetic metal complex is administered, or gamma camera (or SPECT, single photon emission computed tomography) body scanning when a gamma-emitting metal is complexed within the administered texaphyrin. A preferred paramagnetic metal is Gd(III) A preferred diamagnetic metal is Lu(III), In(III) or La(III). A preferred gamma-emitting metal is $^{111}$In(III).

The inherent radiosensitization properties of the texaphyrins allow electromagnetic radiation to be more effective and selective when administered in the vicinity of the texaphyrin. Lower doses of radiation may therefore be used. The radiation may be from an external source or may be from an internal source, such as a radioactive metal bound to a texaphyrin. Examples of a radioactive metal include $^{153}$Gd, $^{111}$In, or $^{90}$Y. Alternatively, a second texaphyrin metal complex having essentially identical biolocalization property and exhibiting the ability to generate singlet oxygen upon exposure to light is administered. The second texaphyrin metal complex is photoirradiated in proximity to the benign or malignant neoplasm cells or atheroma, possibly using fiber optics or laser, to cause neoplasm tissue destruction or atheromatous plaque destruction from the singlet oxygen produced. The metal in the second texaphyrin metal complex is a diamagnetic metal, preferably La(III), Lu(III) or In(III).

A further embodiment is the use of a texaphyrin radiation sensitizer and a photosensitive texaphyrin for treatment. This molecule may be a single texaphyrin diamagnetic metal complex, since the metal is not important for radiosensitization. A synergistic killing of cells may then be achieved by the use of light for photodynamic therapy followed by or in combination with electromagnetic radiation. An alternative embodiment is a synergistic killing due to an intrinsic radiochelated texaphyrin and externally applied radiation. In vitro uses of the method of radiosensitization and radiation therapy include sterilizations, and in the treatment of bone marrow, transfused blood or transplanted organs.

Texaphyrin-metal complexes will be chosen which themselves show a high intrinsic biolocalization selectivity for neoplasms, neoplastic tissues or atheroma. For example, the B2T2 and the T2BET texaphyrins demonstrate in vivo affinity for tissue high in lipid content, atheroma, the liver, kidneys and neoplasms.

The texaphyrin complexes are good candidates for such biomedical radiation sensitizers and photosensitizers. They "soak up" electrons in an irradiated area allowing hydroxyl radicals to cause radiation damage, and the texaphyrin radicals react covalently with neighboring molecules causing further radiation damage. They are easily available, have low intrinsic cytotoxicity, long wavelength absorption, generate singlet oxygen, are soluble in physiological environments, have the ability to be conjugated to site-specific transport molecules, have quick elimination, are stable and are easily subject to synthetic modification. Significant advantages to using texaphyrins for imaging and destruction of cells are:

i) one texaphyrin can be used for both functions;

ii) texaphyrins possess inherent selective biolocalization and have the potential for derivatization to enhance that localization;

iii) since texaphyrins are radiation sensitizers, radiation is more effective and lower doses of radiation may be used, therefore fewer side effects are experienced; and iv) a metal complex is not necessary for radiosensitization.

The present invention provides a method to "see" and "kill" particular cells with a single agent having biolocalization selectivity and radiation-enhancing properties.

EXAMPLE 9

Figure 12A:
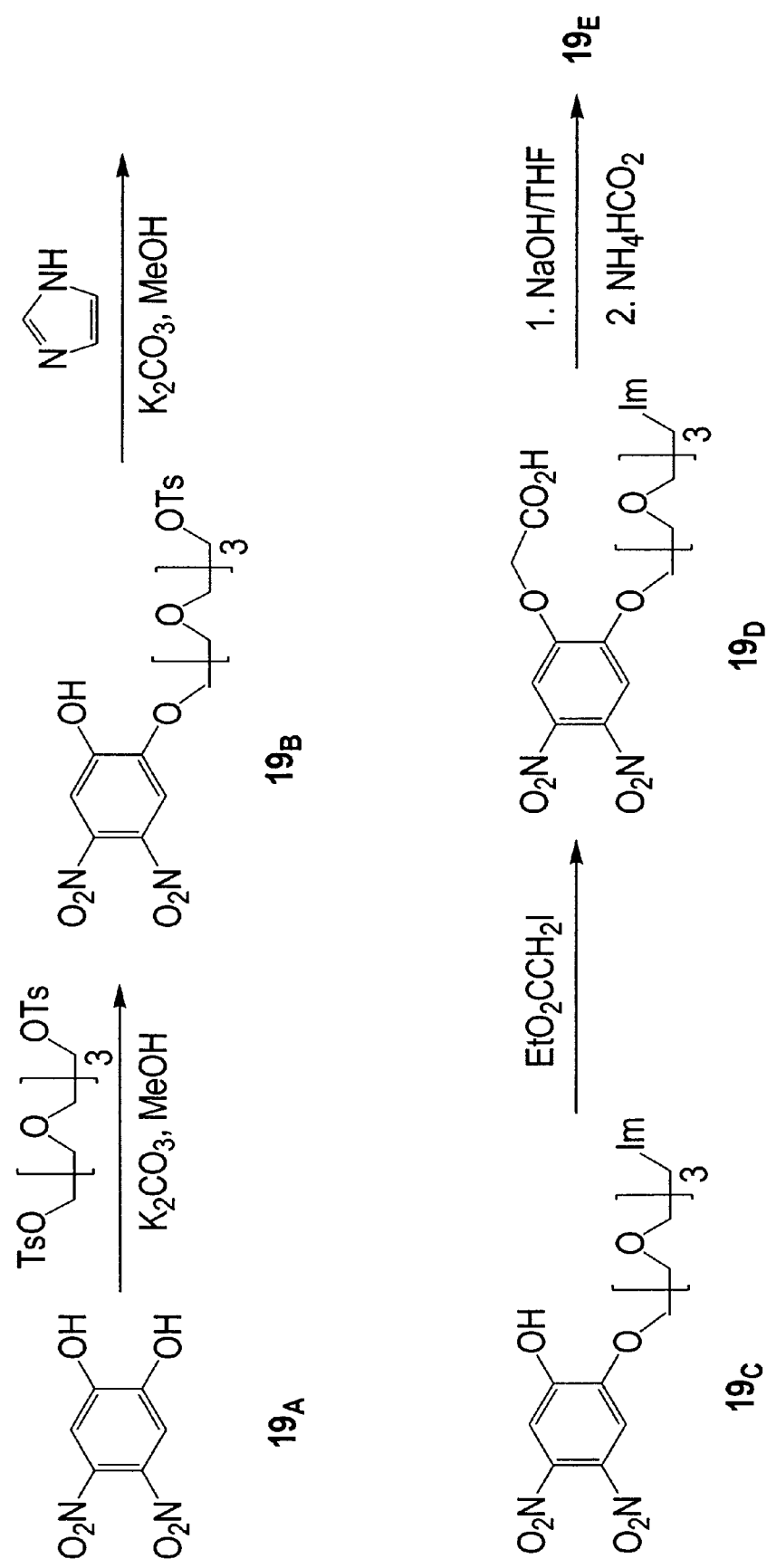
FIGS. 12A and 12B schematically summarize the synthesis of a dysprosium texaphyrin having an imidazole catalytic group.
Figure 12B:
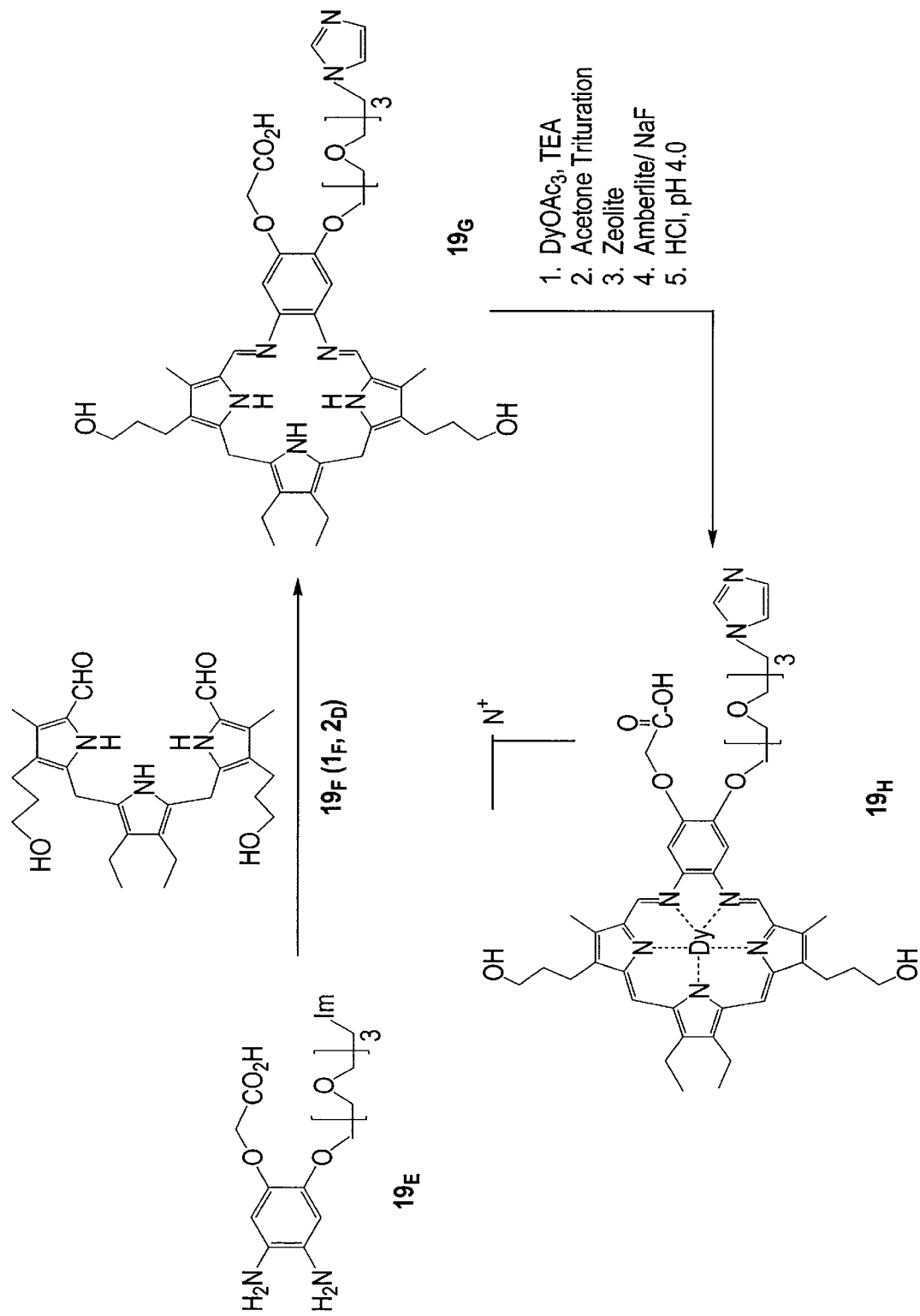

Synthesis of a Dy(III)-Texaphyrin Having an Imidazole Catalytic Group, FIGS. 12A–12B Dysprosium (III) complex of 16-[1-(hydroxy)acetyl-2-oxyl-17-[2-[2-[2-[2-(N-imidazolyl)ethoxy]ethoxy]ethoxy]

ethoxy]-9,24-bis(3-hydroxypropyl)-4,5-diethyl-10,23-dimethyl-13,20,25,26,27-pentaazapentacyclo-[20.2.1.1$^{3,6}$.1$^{8,11}$.0$^{14,19}$]heptacosa-1,3,5,7,9,11(27),12,14(19),15,17,20,22(25),23-tridecaene (19$_H$, FIG. 19B). 4,5-Dinitrocatechol (19$_A$) is reacted with triethylene glycol ditosylate (1 equiv.) in the presence of potassium chloride and methanol. The tripyrrole 19$_F$ can be prepared as described in PCT publication no. WO 94/29316 (PCT appln. US94/06284), the disclosure of which is incorporated herein by reference. The monotosylate (19$_B$) is isolated from the resulting mixture, and is reacted with imidazole (1 equiv.) in the presence of potassium carbonate and methanol to give 4,5-dinitro-2-[2-[2-[2-[2-(N-imidazolyl)ethoxy]ethoxy]ethoxy]ethoxy]phenol (19$_C$). Following the procedures described for the synthetic scheme of FIG. 2A, and as outlined in FIGS. 19A–19B, compound 19$_C$ is reacted with ethyl-2-iodoacetate, and the resulting compound 19$_D$ is saponified and reduced to give the corresponding diamino compound 19$_E$ which is then reacted with tripyrrole 19$_F$. The resulting nonaromatic macrocycle 16-[1-(hydroxy)acetyl-2-oxy]-17-[2-[2-[2-[2-(N-imidazolyl)ethoxy]ethoxy]ethoxy]-9,24-bis(3-hydroxypropyl)-4,5-diethyl-10,23-dimethyl-13,20,25,26,27-pentaazapentacyclo-[20.2.1.1$^{3,6}$.1$^{8,11}$.0$^{14,19}$]heptacosa-3,5,8,10,12,14(19),15,17,20,22,24-undecaene (19$_G$) is metallated to give the Dy(III)Tx complex 19$_H$ having an imidazole as a catalytic group.

The above-described Dy(III)-Tx complex is an example of a texaphyrin complex having an appended catalytic group, imidazole, attached via a tri(ethylene glycol) linker to a texaphyrin metal complex. Such a catalytic group may assist as a general base in site-specific hydrolysis of an RNA target. For this purpose, the texaphyrin metal complex is conjugated to an oligodeoxyribonucleotide complementary in sequence to the RNA being cleaved. The oligo is conjugated to the texaphyrin via a linker group, such as the carboxy group at the 16-position of the Dy(III)Tx compound 19$_H$, following the procedures described herein.

EXAMPLE 10

Figure 13A:
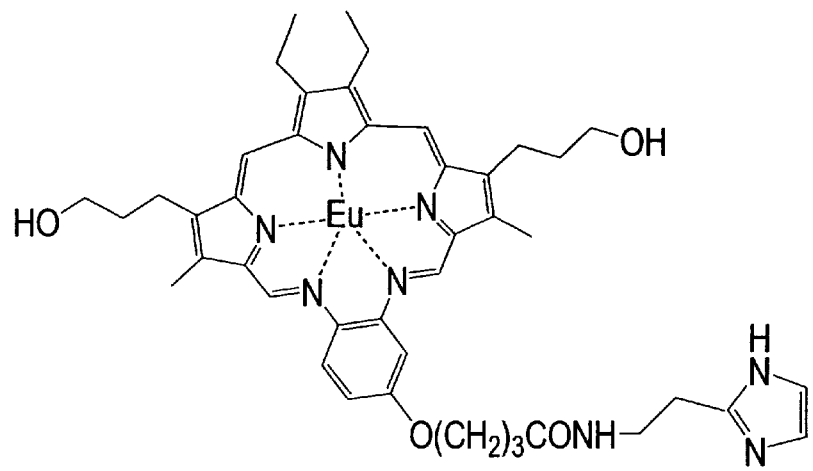
FIGS. 13A and 13B show europium texaphyrins having a histamine group attached (13A) and an arginine methyl ester group attached (13B).
Figure 13B:
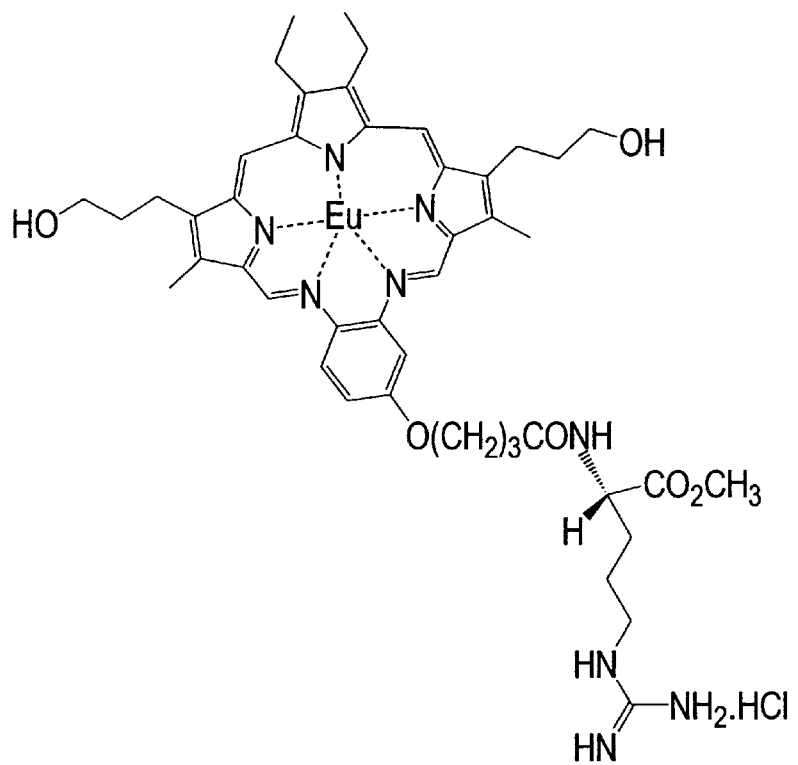

Synthesis of Eu(III)-Texaphyrin Having an Amino Acid or Amino Acid Derivative Catalytic Group, FIGS. 13A–13B Eu(III)-Tx carboxylic acid complex 2$_F$ (n=3, 92 mg, 0.1 mmol) was dissolved in 5 mL of dry purified DMF and cooled to 0° C., after which 1-ethyl-3-(3-dimethylaminopropyl)carbodiimide hydrochloride (EDC; 57 mg, 0.3 mmol) and 0.5 mL of pyridine were added. The resulting activation reaction was allowed to proceed for 1 hr at 0° C. Histamine dichloride (55 mg, 0.3 mmol) was then added, together with 1-hydroxybenztriazole (5 mg) and dimethylaminopyridine (5 mg) in 3 mL of water. The reaction mixture was then stirred for 1 hr at 0° C., followed by stirring at RT for 5 days. The solvents were evaporated off in vacuo at RT and the product was recrystallized from a methanol-benzene mixture to give the final Eu(III)Tx-histamine conjugate shown in FIG. 20A. An analytical sample was prepared by reverse phase column chromatography. UV-Vis (H$_2$O, pH 7): $\lambda_{max}$ (nm): 457.5, 761.5; FAB HR MS: for C$_{43}$H$_{51}$N$_8$O$_4$Eu, calcd.: 896.324571, found: 896.323476.

Following the above-described procedures, L-arginine methyl ester dihydrochloride (78 mg, 0.3 mmol) was reacted with the activated Eu(III)Tx carboxylic acid 2$_F$. The reaction mixture was stirred for 1 hr at 0° C. and then for 5 days, at RT. The solvents were evaporated off and the product recrystallized to give the final Eu(III)Tx shown in FIG. 20B. UV-Vis (H$_2$O, pH 7): $\lambda_{max}$ (nm): 457.0, 761.0; FAB HR MS: for C$_{45}$H$_{58}$ClN$_9$O$_6$Eu, calcd.: 1008.341102, found: 1008.34004.

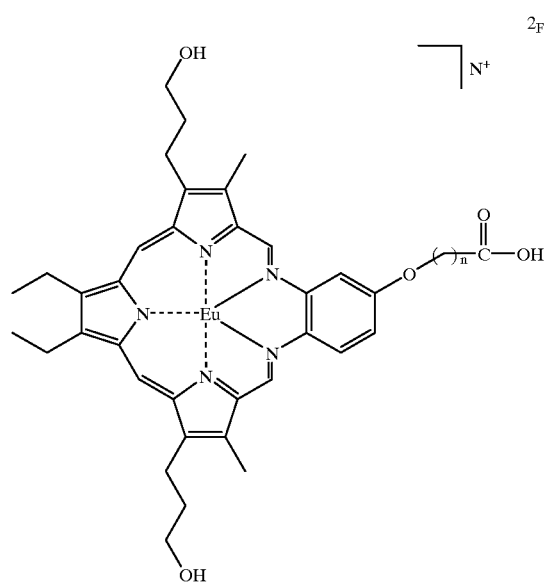

The texaphyrin carboxylic acid complex 2$_F$ may be prepared as described in PCT publication no. WO 94/29316 (PCT appln. US 94/06284), the disclosure of which is incorporated herein by reference.

Following similar procedures, metal complexes of texaphyrin having substituents containing an amine group may be prepared via reaction of the activated acid of the texpahyrin complex with an ainine component of the amine-containing substituent. A general synthetic scheme for the formation of amide-linked derivatives of texaphyrin is presented below and is described in more detail in PCT publication no. WO 94/29316 (PCT appln. US 94/06284), the disclosure of which is incorporated herein by reference. Amine-containing substituents include amine-containing saccharides, polyscaaharides, amino acids, amino acid derivatives, polyamino acids, and the like.

In the following scheme, R=sapphyrin, texaphyrin, porphyrin or a catalytic group; (NH$_2$)$_m$ represents monoamines NH$_2$(CH$_2$)$_x$, x=0–12; diamines NH$_2$—(CH$_2$)$_x$—NH$_2$, x=2–12; triamines (NH$_2$(CH$_2$)$_x$)$_3$N, x=2–6; or tetramines (NH$_2$(CH$_2$)$_x$)$_2$N(CH$_2$)$_y$N((CH$_2$)$_x$NH$_2$)$_2$, x=2–4, y=2–6.

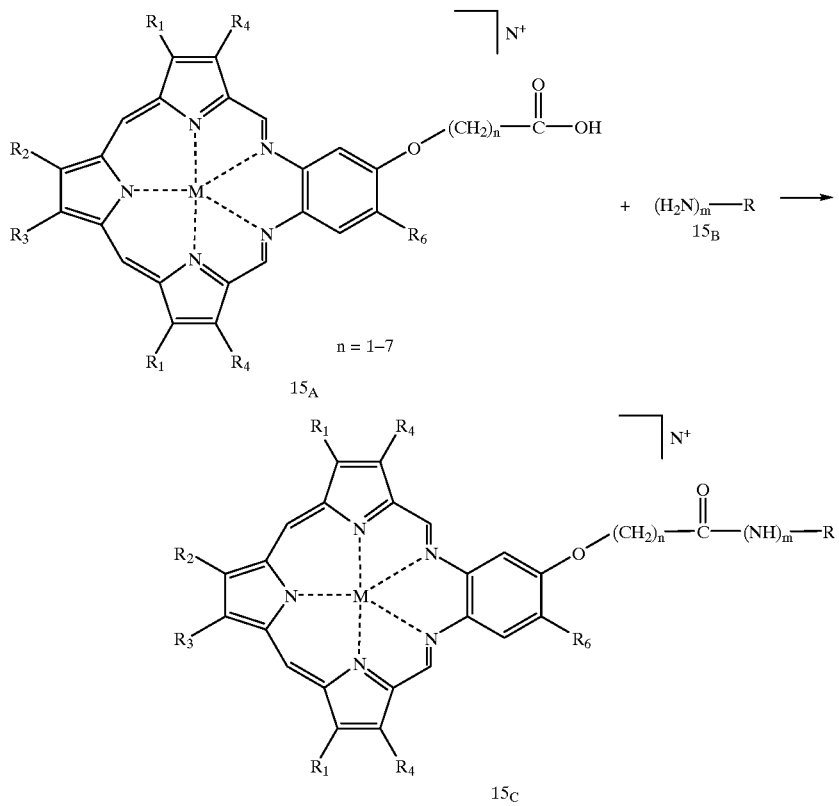

Such amine substituents may function as catalytic groups to assist the texaphyrin metal complex in catalyzing certain reactions.

Catalytic groups may be useful in, for example, the enhancement of NADH or NADPH oxidation reactions. Without being bound by theory, it is believed that such NADH and/or NADPH oxidation is a mode of action for, or otherwise contributes to, the radiation-sensitizing effects exhibited by texaphyrins.

The following references are incorporated in pertinent part by reference herein for the reasons cited below.

REFERENCES

Adams, G. E., and Dewey, D. L., *Biochem. Biophys. Res. Commun.*, 12:473–477 (1963).
Agrawal, S., and Tang, J. Y., Tetrahedron Letters, 31:7541 (1990).
Ash, D. V et al. Br. *J. Cancer* 40:883–889 (1979).
Beard, C. J. et al. *Cancer: Principles & Practice of Oncology*, 4th ed:2701 (1993).
Brock, W. A. et al. *Can. Bull.*, 39(2):98 (1987).
Brown, J. M. *Modification of Radiosensitivity in Cancer Treatment* 139–176 (1984).
Bush, R. S. et al Br. *J. Cancer* 37 (Suppl) 302–306 (1978).
Caracciolo et al., *Science*, 245:1107 (1989).
Chapman, D. L. et al. *Int. J. Radiat. Oncol. Biol. Phys.* 26:383–389 (1974).
Coleman, C. N. et al. *Int. J. Radiat. Oncol. Biol. Phys.* 10:1749–1743 (1984).
Coleman, C. N. et al. *Int. J. Radiait. Oncol. Biol. Phys.* 12:1105–1108 (1986).
Coleman, C. N. et al. *Cancer Res.* 47:319–322 (1987).
Denekamp, J. et al. *Br. J. Cancer* 41:1–9 (1980).
Dische, S. et al. *Br. J. Cancer* 567–579 (1977).
Dische, S. et al. *Int. J. Radiat. Oncol. Biol. Phys.* 5:851–860 (1979).
Dische, S. et al. *Br. J. Radiol.* 59: 911–917 (1986).
Furuta et al., *J. Am. Chem. Soc.*, 113:4706–4707 and 6677–6678 (1991).
Goodchild, J., *Bioconjugate Chemistry.*, 1:165–187, (1990).
Hendrickson, F. R. and Withers, H. R *American Cancer Society Textbook of Clinical Oncology* 35–37 (1991).
Hill, B. T., *Can. Treat. Rev.*, 18:149 (1991).
Horwich, A. et al. *Int. J. Radiat. Oncol. Biol. Phys.* 59: 1238–1240 (1986).
Kallman, R. F. *Radiology* 105:135–142 (1972).
Kinsella, T. J. *J. Clin. Oncol.* 2:11.44–1150 (1984a).
Kinsella, T. J. *Int. J. Radiat. Oncol. Biolo. Phys.* 10:69–76 (1984b).
Kinsella, T. J. *Int. J. Radiat. Oncol. Biol. Phys.* 11:1941–1946 (1985).
Mulcahy, R. T. et al. *Clinical Oncology: A multidisciplinary approach for physicians and students*, 4th ed. 87–90 (1993).
Newman, H. F. V. et al. *Int. J. Radiat. Oncol. Biol. Phys.* 12:1113–1116 (1986).
Newman, H. F. V. et al. *Int. J. Radiat. Oncol. Biol. Phys.* 15:1073–1083 (1988).
Roberts, J. T. et al. *Int. J. Radiat. Oncol. Biol. Phys.* 10:1755–1758 (1984).
Rubin, P. and Siemann, D. W. *Clinical Oncology: A multidisciplinary approach for physicians and students* 87–88 (1993).
Saunders, M. I. et al. *Int. J. Radiat. Oncol. Biol. Phys.* 10:1759–1763 (1984).
Shenoy, M. A. and Singh, B. B. *Cancer Invest.* 10:533–551 (1992).

Tannock, I. F. *Br. J. Radiol.* 45:515–524 (1972).
Thomlinson, R. H. et. al. 27:167–174 (1976).
Urtasun, R. C. et al. *Br. J. Cancer* 37 Suppl. III 271–275 (1978).
Wang, C. C. *Clinical Radiation Oncology: Indications, Techniques and Results* (1988).
Wasserman, T. H. et al. *Int. J. Radiat. Oncol. Biol. Phys.* 5:775–786 (1979).
Watson, E. R. et al. *Br. J. Radiol* 51:879–887 (1978).
Workman, P. et al. *Int. J. Radiat. Oncol. Biol. Phys.* 17:177–181 (1989).
*J. Org. Chem.*, 55:4693–4699, (1990).
Sessler et al., *SPIE Proc. Soc. Opt. Eng.*, 1426:318–329, (1991).
Sessler et al., *J. Am. Chem. Soc.* 114:8704 (1992).
Townsend, A. J., Cowan, K. H., *Can. Bull.*, 41(1):31 (1989).
U.S. Pat. No. 5,159,065.
U.S. Pat. No. 5,120,411.
U.S. Pat. No. 5,041,078.
Wang et al., *Can. J. Chem.*, 55:4112 (1977).

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A texaphyrin-biomolecule conjugate, wherein the texaphyrin is hydroxylated.
2. A texaphyrin-biomolecule conjugate, wherein the texaphyrin is water-soluble.
3. A texaphyrin-biomolecule conjugate wherein the texaphyrin is represented by the following structure:

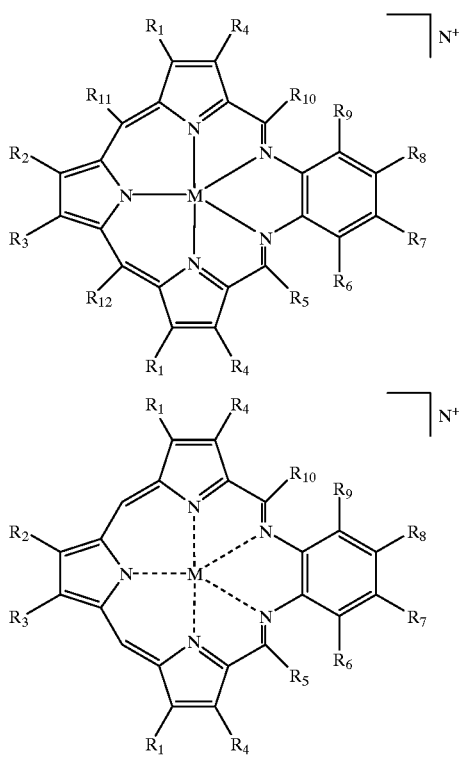

where,

M is a divalent metal cation or a trivalent metal cation;

$R_1$–$R_4$, $R_7$ and $R_8$ are independently hydrogen, hydroxyl, alkyl, aryl, hydroxyalkyl, oxyalkyl, oxyhydroxyalkyl, saccharide, carboxyalkyl, carboxyamidealkyl, a biomolecule, or a couple to a biomolecule; where at least one of $R_1$, $R_7$ and $R_8$ is oxyhydroxyalkyl, saccharide, oxyalkyl, carboxyalkyl, carboxyamidealkyl, or hydroxyalkyl having at least one hydroxy substituent, and provided that $R_7$ is the same as $R_8$;

$R_5$, $R_6$, $R_9$ and $R_{10}$ are hydrogen; and

N is zero, 1 or 2;

provided that, at least one of $R_1$–$R_4$, $R_7$ and $R_8$ is a biomolecule or a couple to a biomolecule.

4. The conjugate of claim 3 where the metal cation is a divalent metal cation selected from the group consisting of Ca(II), Mn(II), Co(II), Ni(II), Zn(II), Cd(II), Hg(II), Fe(II), Sm(II) and UO₂(II), or a trivalent metal cation selected from the group consisting of Mn(III), Co(III), Ni(III), Fe(III), Ho(III), Ce(III), Y(III), In(III), Pr(III), Nd)III), Sm(III), Eu(III), Gd(III), Tb(III), Dy(III), Er(III), Tm(III), Yb(III), Lu(III), La(III), and U(III).

5. The conjugate of claim 1 where the biomolecule is an antibody.

6. The conjugate of claim 2 where the biomolecule is an antibody.

7. The conjugate of claim 3 where the biomolecule is an antibody.

8. The conjugate of claim 3 where $R_1$ is alkyl or hydroxyalkyl, and each of $R_2$, $R_3$ and $R_4$ is alkyl.

9. The conjugate of claim 3 where $R_1$ is $CH_2CH_3$ or $CH_2CH_2CH_2OH$, each of $R_2$ and $R_3$ is $CH_2CH_3$, and $R_4$ is $CH_3$.

10. The conjugate of claim 3 where $R_7$ and $R_8$ are the same.

11. The conjugate of claim 3 where $R_7$ is $OCH_2CH_2CH_2OH$ and $R_8$ is a biomolecule or a couple to a biomolecule.

12. The conjugate of claim 3 where $R_7$ is $O(CH_2CH_2O)_2 CH_2CH_2OCH_3$ and $R_8$ is a biomolecule or a couple to a biomolecule.

13. The conjugate of claim 3 where M is a lanthanide metal cation.

14. The conjugate of claim 3 where $R_1$ is $CH_2CH_3$ or $CH_2CH_2CH_2OH$; each of $R_2$ and $R_3$ is $CH_2CH_3$; $R_4$ is $CH_3$; each of $R_5$, $R_6$, $R_9$ and $R_{10}$ is H; $R_7$ is H, $CH_3$, $OCH_3$, $O(CH_2)_n COOH$, $OCH_2CH_2CH_2OH$ or $O(CH_2CH_2O)_n CH_3$ where n is 1–7; and $R_8$ is a biomolecule or a couple to a biomolecule.

15. The conjugate of claim 3 where M is a lanthanide metal cation; $R_1$ is $CH_2CH_3$ or $CH_2CH_2CH_2OH$; each of $R_2$ and $R_3$ is $CH_2CH_3$; $R_4$ is $CH_3$; each of $R_5$, $R_6$, $R_9$ and $R_{10}$ is H; $R_7$ is H, $CH_3$, $OCH_3$, $O(CH_2)_n COOH$, $OCH_2CH_2CH_2OH$ or $O(CH_2CH_2O)_n CH_3$ where n is 1–7; and $R_8$ is a biomolecule or a couple to a biomolecule.

16. The conjugate of claim 3 where M is a lanthanide metal cation; $R_1$ is $CH_2CH_3$ or $CH_2CH_2CH_2OH$; each of $R_2$ and $R_3$ is $CH_2CH_3$; $R_4$ is $CH_3$; each of $R_5$, $R_6$, $R_9$ and $R_{10}$ is H; $R_7$ is $OCH_2COOH$; and $R_8$ is a biomolecule or a couple to a biomolecule.

17. The conjugate of claim 3 where M is a lanthanide metal cation; $R_1$ is $CH_2CH_3$ or $CH_2CH_2CH_2OH$; each of $R_2$ and $R_3$ is $CH_2CH_3$; $R_4$ is $CH_3$; each of $R_5$, $R_6$, $R_9$ and $R_{10}$ is H; $R_7$ is $O(CH_2CH_2O)_3 CH_3$; and $R_8$ is a biomolecule or a couple to a biomolecule.

* * * * *